US007017389B2

(12) United States Patent
Gouma

(10) Patent No.: US 7,017,389 B2
(45) Date of Patent: Mar. 28, 2006

(54) SENSORS INCLUDING METAL OXIDES SELECTIVE FOR SPECIFIC GASES AND METHODS FOR PREPARING SAME

(75) Inventor: Pelagia-Irene Gouma, Port Jefferson, NY (US)

(73) Assignee: The Research Foundation of SUNY at Stony Brook, Stony Brook, NY (US)

( * ) Notice: Subject to any disclaimer, the term of this patent is extended or adjusted under 35 U.S.C. 154(b) by 0 days.

(21) Appl. No.: 10/419,349

(22) Filed: Apr. 21, 2003

(65) Prior Publication Data

US 2003/0217586 A1    Nov. 27, 2003

Related U.S. Application Data

(60) Provisional application No. 60/374,189, filed on Apr. 20, 2002.

(51) Int. Cl.
  *G01N 7/00* (2006.01)
(52) U.S. Cl. .................. 73/31.05; 73/31.06; 422/83
(58) Field of Classification Search ............... 73/31.05, 73/31.06; 422/83
  See application file for complete search history.

(56) References Cited

U.S. PATENT DOCUMENTS

| | | | | |
|---|---|---|---|---|
| 3,953,173 A | * | 4/1976 | Obayashi et al. | 73/25.03 |
| 4,007,063 A | * | 2/1977 | Yasuda et al. | 148/284 |
| 4,030,340 A | * | 6/1977 | Chang | 73/31.01 |
| 4,169,369 A | * | 10/1979 | Chang | 73/31.06 |
| 4,430,191 A | * | 2/1984 | Sone et al. | 204/401 |
| 4,481,499 A | * | 11/1984 | Arima et al. | 73/31.06 |
| 5,546,004 A | | 8/1996 | Schmelz | |
| 5,858,186 A | | 1/1999 | Glass | |
| 5,969,231 A | * | 10/1999 | Qu et al. | 73/31.05 |
| 5,993,625 A | * | 11/1999 | Inoue et al. | 204/425 |
| 6,173,602 B1 | | 1/2001 | Moseley | |

OTHER PUBLICATIONS

Imawan et al., "Gas-sensing characteristics of modified-$MoO_2$ thin films using Ti-overlayers for $NH_3$ gas sensors", *Sensors and Actuators* B 64 (2000) pp. 193-197.

Imawan et al., "A new preparation method for sputtered $MoO_3$ multilayers for the application in gas layers", *Sensors and Actuators* B 78 (2001) pp. 119-125.

Ferroni et al., "Nanosized thin films of tungsten-titanium mixed oxides as gas sensors", *Sensors and Actuators* B 58 (1999) pp. 289-294.

Chung et al., "Gas sensing properties of $WO_3$ thick film for $NO_2$ gas dependent on process condition", *Sensors and Actuators* B 60 (1999) pp. 49-56.

Marquis et al., "A semiconducting metal oxide sensor array for the detection of $NO_x$ and $NH_3$", *Sensors and Actuators* B 77 (2001) pp. 100-110.

Sberveglieri et al., "$WO_3$ sputtered thin films for $NO_x$ monitoring", *Sensors and Actuators* B 26 (1995) pp. 89-92.

Livage et al., "Encapsulation of biomolecules in silica gels", *J. Phys.: Condens.* Matter 13 (2001) pp. R673-R691.

* cited by examiner

*Primary Examiner*—Hezron Williams
*Assistant Examiner*—André K. Jackson
(74) *Attorney, Agent, or Firm*—Dilworth & Barrese, LLP

(57) ABSTRACT

Sensors are provided which are selective for a specific gas. The sensors include a substrate, electrodes, and a thin film metal oxide. Methods for choosing the metal oxide to be utilized in the sensor with selectivity for the specific gas are also provided, as are methods for determining the presence of a specific gas in a gaseous mixture.

14 Claims, 23 Drawing Sheets

(a)            (b)

Reaction of urea with urease releases ammonia that is sensed by $MoO_3$ porous film $(H_2N)_2CO$ ——in the presence of urease→ $2NH_4^+ + HCO_3^-$ where $2NH_4^+ + OH^- \rightarrow 2NH_3 + H_2O$ and $HCO_3^- + H_2 \rightarrow CO_2 + H_2O$

- $MoO_3$
- urea
- urease
- pores
- electrodes

SENSORS INCLUDING METAL OXIDES SELECTIVE FOR SPECIFIC GASES AND METHODS FOR PREPARING SAME

CROSS REFERENCE TO RELATED APPLICATIONS

This application claims the benefit under 35 U.S.C. § 119(e) of earlier filed and copending U.S. Provisional application No. 60/374,189 filed Apr. 20, 2002, the contents of which are incorporated by reference herein.

BACKGROUND OF THE INVENTION

1. Technical Field

The present invention relates to sensors for determining the concentration of gases. More particularly, the present invention provides methods which permit the selection of a specific metal oxide which, in turn, is selective in its sensitivity to a specific gas. A sensor, which includes the metal oxide in the form of a thin film in conjunction with a substrate and electrodes, may then be produced which is capable of rapidly detecting very low concentrations of the specific gas with reduced interference from other gases. The sensors thus produced may be utilized in measuring gases in a variety of settings, including automotive and biological applications.

2. Background of Related Art

Sensors are utilized in a variety of applications to determine the presence of gases. For example, ammonia sensors are being used in diverse applications such as food technology, chemical plants, medical diagnosis, and environmental protection. There are several challenges associated with the development of sensor technology for monitoring gases, such as those found in combustion processes or in biological systems. With respect to combustion processes, the challenges include high temperatures, presence of reducing and oxidizing gases, organic vapors (VOCs), high flow rates, etc. With biological systems, challenges include sensitivity to extremely low levels of gases, presence of reducing and oxidizing gases, organic vapors (VOCs), etc. One of the more difficult challenges in these processes is achieving selectivity for a specific compound or gas.

Metal oxides have been utilized in sensors for some time. These oxides may be found as several different crystallographic phases with identical chemical compositions but different crystal structures (polymorphs). Metal oxides used in sensors include, for example, titanium dioxide ($TiO_2$), tungsten trioxide ($WO_3$), molybdenum trioxide ($MoO_3$), vanadium pentoxide ($V_2O_5$), zirconium dioxide ($ZrO_2$), niobium pentoxide ($Nb_2O_5$), iridium dioxide ($IrO_2$), tantalum oxide ($Ta_2O_3$), and combinations thereof.

Sensors frequently use semiconductors for the qualification and/or quantification of a compound or substance being detected. There are two basic types of semiconductors: n-type, in which the density of holes in the valence band is exceeded by the density of electrons in the conduction band; and p-type, in which the density of electrons in the conduction band is exceeded by the density of holes in the valence band.

There have been many reports on p-n type transitions occurring during the testing of resistive type sensors. The conductivity of a semiconductor can be represented in terms of the carrier density and mobility of the individual charge carriers by equation (1)

$$\sigma = qn\mu_n + qp\mu_p \qquad (1)$$

where n and p are the number of electron and hole carriers respectively, q is the charge associated with the charge carrier and the μ values represent the corresponding mobilities. All four parameters are dependent on temperature and the values of n and p, which determine whether it is an n-type or p-type semiconductor, vary with the generation of inter-band traps due to the formation of vacancies or impurity substitution.

For example, $MoO_3$ is an n-type semiconductor in the stable state. In a metastable state, however, oxygen vacancies may exist in different proportions leading to either excess electrons near the conduction band or holes near the valence band. A typical oxygen vacancy formation may be represented by the following quasi-chemical reaction (2):

$$O_o^* \leftrightarrows \tfrac{1}{2}O_2(g) + V_o^{2+} + 2e^- \qquad (2)$$

Where $O_o^*$ represents an unstable oxygen atom in an oxygen site and $V_o^{2+}$ represents an oxygen vacancy with double positive charge.

When oxygen is incorporated into these vacancies, a reversible reaction (3) occurs as shown below.

$$[V_o^{2+}] + \tfrac{1}{2}O_2 \leftrightarrows O_o + 2h^+ \qquad (3)$$

When the hole concentration drops below a threshold value or when equation (2) is favored to equation (3), p to n shift occurs due to formation of donors near the conduction band.

The simple nature of the sensing mechanism of semiconducting oxide gas sensors often results in a given oxide system being sensitive to more than one type of gases, which causes undesirable gas interference effects to the sensing behavior of the sensor. For example, previous efforts investigating the sensing response of $MoO_3$ to various gases in the temperature range of 250° C. to 475° C. have revealed that $MoO_3$ was more sensitive to $NH_3$ than to $NO_2$ and $H_2$ at 425° C. and that the gas sensitivity dropped with decreasing film thickness (<300 nm). Multilayer sputter processing of $MoO_3$ resulted in improved $H_2$ sensing properties and low cross-sensitivity towards $NH_3$. See Imawan et al., *Sensor Actuat B-Chem*, 78, pp. 119–125 (2001). Others have reported the enhancement of sensitivity and selectivity to $NH_3$ following the addition of Ti overlayers to $MoO_3$, and to $H_2$, by adding $V_2O_5$ to $MoO_3$ (Imawan et al., *Sensor Actuat B-Chem*, 64, pp. 193–197 (2000)), while others have reported sensitivity towards CO for Ti additions to $MoO_3$. Ferroni et al., *Sensor Actuat B-Chem*, 58, pp. 289–294 (1999).

Similarly, there have been numerous reports of $WO_3$ sensors for $NO_x$ detection. Some reports describe thick film $WO_3$ sensors that are sensitive to $NO_2$ at 100° C., but these films showed a very weak response to $NO_2$ above 250° C. and the response was found to be p-type at higher temperatures (>250° C.). Chung et al., *Sensor Actuat B-Chem*, 60, pp. 49–56 (1999). Other workers have fabricated sensor arrays for the selective detection of $NO_2$ and $NH_3$; these sensors were operable at optimum temperatures of 300° C. and 350° C. and utilized dopants to achieve selectivity (Marquis et al., *Sensor Actuat B-Chem*, 77, pp. 100–110 (2001)). Still others report $WO_3$ thin films sputter deposited at 350° C. have shown good response to $NO_x$ at 400° C. Sberveglieri et al., *Sensor Actuat B-Chem*, 26, pp. 89–92 (1995).

The addition of dopants and other treatments, such as heating, are widely used approaches to stabilize metal oxides used in sensors. For example, U.S. Pat. No. 6,173,602 describes a transition metal oxide gas sensor which includes a substoichiometric molybdenum trioxide of formula $MoO_{3-x}$ wherein $MoO_3$ has been reduced by a thermal treatment or by substituting some of the molybdenum with a metal with a principal valence of less than six in order to stabilize the structure of the substoichiometric phase ($MoO_{3-x}$).

Efforts are underway to develop sensors that are selective in their response to specific particular gases. These sensors could have use in numerous fields, including automotive and similar combustion applications, biological monitoring systems, environmental monitoring systems, etc.

In the automotive field, ammonia(urea)/Selective Catalytic Reduction (SCR) is one of the leading $NO_x$ emission reduction systems under consideration for diesel and lean-burn engines. SCR systems are employed in the exhaust systems of vehicles, composition systems in power plants, and in industrial boilers to monitor emissions of $NO_2$ and NO. These gases are harmful by-products of combustion processes.

In a SCR converter, ammonia serves as a reducing agent for nitrogen oxides, such as nitrogen dioxide, converting them into environmentally safe nitrogen and water vapor. Adjusting the requisite stoichiometric ratio of nitrogen oxides to ammonia, or to some substance such as urea that can be converted into ammonia, can be done with satisfaction only if the nitrogen oxide concentration in the exhaust or flue gas can be measured. A selective ammonia sensor located downstream of the SCR catalyst may be utilized to calculate the amount of un-reacted and excess ammonia, which is fed into the inlet stream, thus minimizing possible ammonia and $NO_x$ emissions. Similarly, a sensor able to detect $NO_2$ in the presence of $NH_3$ would be extremely useful.

SCR systems have the potential to reduce $NO_x$ emissions by more than 90% with little impact on fuel economy. As the 2007 Tier II emission standards promulgated by the United States Environmental Protection Agency require over 90% $NO_x$ conversion, the automotive industry is actively developing control systems utilizing urea/SCR to meet these future standards. Transient control of the ammonia injection system is an essential part of the overall control system utilizing urea/SCR.

U.S. Pat. No. 5,546,004 describes a sensor for SCR systems used to measure the concentration and adjust the ratio of ammonia (urea) to nitrogen oxides. The sensing device is a non-selective sensing device in which oxide dopants are added to improve its sensitivity to ammonia, with titanium dioxide functioning as the main sensor material. Pairs of electrical contacts are disposed throughout the sensor material, with a course of concentration of an adsorbent being determined as a function of its penetration into the sensor material.

Biosensors are electronic devices used to detect the presence and determine the concentration of substances of biological interest. The use of enzymes in bio-detection adds selectivity to the sensing process (e.g. glucose oxidase membranes are used to monitor glucose levels of diabetics). See, e.g., Livage, et al., "Encapsulation of biomolecules in silica gels", *J. Phys.: Condens. Matter*, 13, pp. R673–R691, 2001.

For example, U.S. Pat. No. 5,858,186 discloses a urea biosensor for hemodialysis monitoring where the sensor is based upon measurement of the pH change produced in an aqueous environment by the products of the enzyme-catalyzed hydrolysis of urea.

The sensitivity and selectivity of a biosensor depends upon the biologically active material, or receptor, included therewith. Suitable receptors for use in biosensors include enzymes, antibodies, lipid layers, cells etc. One drawback with current biosensors is the transducer, or detector, is often not selective, and thus false readings are common.

Current advances in the field of chemical sensing focus on liquid phase chemical detectors/biochemical devices, as well as optical and opto-electronic sensors, polymer-based or silicon-based. These competing sensor technologies primarily operate at temperatures ranging from room temperature to 250° C. and in relatively clean environments. However, sensors are still needed that are capable of operating at high temperatures (>400° C.) and in harsh conditions, e.g., those which prevail in catalytic processes involving nitrogen dioxide and ammonia synthesis or reduction.

Commercially available ammonia sensors suitable for use in the automotive exhaust environment are not yet available. Similarly, economical biosensors which are sensitive, selective, and stable are not readily available. Therefore, the development of selective sensors would be very important for development of these systems. Such a sensor should be inexpensive, and simple to fabricate and use.

SUMMARY OF THE INVENTION

The present invention is directed to methods for utilizing crystalline forms of metal oxides in sensors which are highly selective for a specific gas. The methods of the present invention permit the selection of a crystalline form of a metal oxide that is selective in its sensitivity to a specific gas. Thus, the methods of the present invention may be utilized to tailor a sensor that will be sensitive to a specific gas, even where the specific gas is present in a gaseous mixture to be analyzed.

The method for selecting the metal oxide having selectivity for a specific gas generally involves the steps of: determining the reducing or oxidizing nature of a specific gas to classify the gas; classifying a metal oxide on the basis of its crystal structure; analyzing the specific gas-metal oxide interactions at the crystal structure's surface; and selecting the metal oxide with the crystal structure possessing a surface most likely to react with the specific gas.

Gases which may be detected in accordance with the present invention may be classified into one of three categories. Type I gases are nitrogen-lacking reducing gases including, but not limited to, CO, alcohols, and hydrocarbons, such as methane, propylene. Type II gases are nitrogen-containing reducing gases including, but not limited to, $NH_3$ and amines. Finally, Type III gases are oxidizing gases including, but not limited to, $O_2$, NO, $NO_2$ etc.

In accordance with the present invention, metal oxides may be classified in one of three categories: "rutile structured" metal oxides; "rhenium oxide structured" or "$ReO_3$-type" metal oxides; and "$\alpha$-$MoO_3$-type" metal oxides.

As used herein, "rutile structured" metal oxides are understood to be those metal oxides possessing a rutile structure similar to that found in $TiO_2$ crystals. The rutile structure is tetragonal, but in some cases it has been described as a distorted hexagonal close packed oxide array with half the octahedral sites occupied by the metal.

As used herein, "rhenium oxide structured" or "$ReO_3$-type" metal oxides possess a cubic structure akin to that found for rhenium oxide ($ReO_3$) crystals, which is closely related to the structure found in perovskite ($CaTiO_3$). The unit cell of the crystal contains metal atoms at the corners with oxygen at the center edges.

As used herein, "$\alpha$-$MoO_3$-type" metal oxides have a unique, weakly bonded 2D layered structure found in the $\alpha$-phase of $MoO_3$ crystals.

Once selected, the crystalline forms of the metal oxides are applied as thin films to a substrate and electrodes to form a sensor for a specific gas. The thin film metal oxides utilized in the sensors do not require the presence of a dopant to attain their selectivity for the specific gas. Preferably, the thin film metal oxides are substantially pure.

As used herein, the term "gas" preferably embraces a gas as such and any material that may be present in a gaseous phase, one example of which is a vapor.

As used herein, "substantially pure" means the thin film metal oxide lacks any additive or dopant to enhance its selectivity for a particular gas. Preferably, a thin film metal oxide is substantially pure if no dopant or other material is added, or if the metal oxide has been not treated, for example by heating, for the purpose of stabilizing any particular crystalline form of such metal oxide.

The present invention is also directed to novel sensors for determining the concentration of a specific gas in a gas or gaseous mixture. The sensors of the present invention are resistive gas detectors that rapidly detect, within seconds, very low concentrations of specific gases with reduced interference from other gases. The sensors of the present invention include a thin film metal oxide capable of exhibiting a response in the form of an increase or a decrease in an electrical property of the film in the presence of the selected gas, while exhibiting little or no response to other gases present in the gaseous mixture sample.

The sensors of the present invention include a substrate, a plurality of electrodes, and a thin film metal oxide. The substrate may be any material suitable for use in a gaseous sensor, such as $Si/SiO_2$, $SiC$, $GaN$, or $Al_2O_3$. In one preferred embodiment, the substrate comprises alumina.

Preferably, the thin film metal oxide is provided with two or more electrodes in communication with the thin film metal oxide, and the thin film metal oxide may be arranged so as to be capable of being contacted with a gas or gaseous mixture to be analyzed. The electrical resistance measured at the electrodes provides a means for calculating the concentration of the selected gas in the gaseous mixture being tested. The electrodes may be made of any material suitable for use in sensors, such as gold, silver, tungsten, chromium, and titanium. In a preferred embodiment, the electrodes are gold.

A sensor in accordance with the present invention may be used as a sensor for the selected gas in quantitative and/or qualitative determinations with gases or gaseous mixtures. The electrodes may be in direct communication with the thin film metal oxide. The sensor may also include a temperature sensing means.

In one embodiment, an ammonia sensor is provided which utilizes a substrate, preferably aluminum oxide, coated with a thin film metal oxide, preferably the alpha phase of molybdenum trioxide ($\alpha$-$MoO_3$). Electrodes, preferably gold, are placed between the aluminum substrate and $MoO_3$ coating.

In another embodiment, a nitrogen dioxide sensor is provided which utilizes a substrate, preferably aluminum oxide, coated with a thin film metal oxide, preferably tungsten trioxide ($WO_3$). Electrodes, preferably gold, are placed between the aluminum substrate and $WO_3$ coating.

In another embodiment, a nitrogen dioxide sensor is provided which utilizes a substrate, preferably aluminum oxide, coated with a thin film metal oxide, preferably the beta phase of molybdenum trioxide ($\beta$-$MoO_3$). Electrodes, preferably gold, are placed between the aluminum substrate and $MoO_3$ coating.

The present invention is also directed to methods for making sensors selective for a specific gas. These methods include the following steps: determining the reducing or oxidizing nature of a specific gas to classify the gas; classifying a metal oxide on the basis of its crystal structure; analyzing the specific gas-metal oxide interactions at the crystal structure's surface; selecting the metal oxide with the crystal structure possessing a surface most likely to react with the specific gas; providing a substrate for the sensor; providing plural electrodes; and, applying the metal oxide to the substrate and plural electrodes as a thin film metal oxide in contact with each electrode, wherein the thin film metal oxide exhibits a response in the form of an increase or a decrease in an electrical property of the thin film metal oxide in the presence of the specific gas.

The present invention is also directed to methods for determining the presence of a specific gas in a gaseous mixture. In accordance with these methods, a gas sensor with plural electrodes is provided, each electrode in contact with a thin film metal oxide which exhibits an increase or a decrease in an electrical property of the thin film metal oxide in the presence of the specific gas. The sensor is placed in contact with the gaseous mixture, an increase or decrease in the electrical property of the electrodes is detected, and the change in electrical property is measured permitting the determination of the specific gas and/or its concentration. Preferably, both the thin film metal oxide and electrodes are in contact with the same gaseous mixture.

The electrical property which may be measured may be the resistance of the sensor, the capacitance of the sensor, and/or the impedance of the sensor.

It will be appreciated that the resistance and/or capacitance, and/or impedance of the thin film metal oxide depends upon the gas or gaseous mixture contacting the thin film metal oxide. Thus, by measuring the resistance and/or capacitance, and/or impedance of the gas sensitive material, the composition of a gas or gaseous mixture can be sensed.

The resistance and/or conductance, and/or impedance may be measured directly. Alternatively, the measurement may be carried out indirectly by incorporating the sensor in a feedback circuit of an oscillator such that the oscillator frequency varies with composition of the gas or gaseous mixture. Gas composition may then be determined using an electronic counter. The signal thus produced may be used to modulate a radio signal and thereby be transmitted over a distance (e.g. by telemetry or as a pulse train along an optical fiber).

Preferably, the thin film metal oxide has sufficient porosity to give a satisfactory surface area for contact with the gas or gaseous mixture sampled.

BRIEF DESCRIPTION OF THE DRAWINGS

FIG. 8a is the spectra of the Mo (3d) peak after exposure to 1000 ppm $NH_3$ in 10% $O_2$; FIG. 8b is the Mo (3d) spectra after exposure to 10% $O_2$ only; FIG. 8c is the spectra after exposure to 1000 ppm $NH_3$ in 0.5% $O_2$; FIG. 8d is the spectra after 1000 ppm $C_3H_6$ in 10% $O_2$ (this spectra was taken after re-oxidizing the film in 10% $O_2$).

FIG. 12 are graphs depicting the response of ion beam deposited $MoO_3$ to ammonia at 450° C.

FIG. 13 is a series of graphs demonstrating the response of sol-gel $MoO_3$ films to $NH_3$ and $NO_2$.

DETAILED DESCRIPTION OF THE INVENTION

Figure 1:
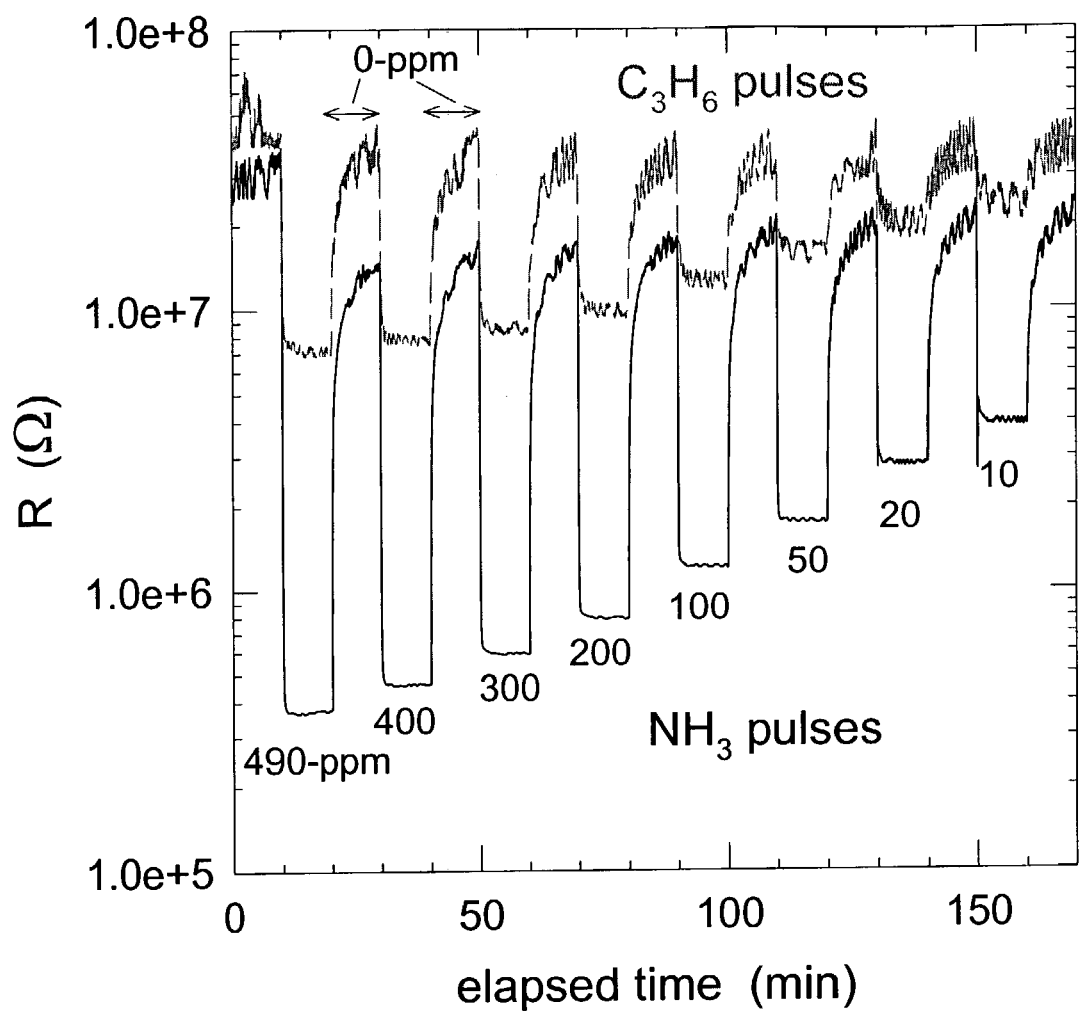
FIG. 1 is a graph demonstrating the variation in resistance with time for a $MoO_3$ film at 438° C. for separate sequences of $NH_3$ and $C_3H_6$ gas pulses. Each 10 minute pulse was separated by 10 minute intervals of 0 ppm concentration of gas. The accompanying oxygen concentration was 10%, with the balance of the gas $N_2$.

The present invention is directed to methods for selecting metal oxides for use in sensors which are highly selective for a specific gas. Selection of the appropriate metal oxide is based on the crystalline structure of the metal oxide, which may be utilized to determine the selectivity of the metal oxide to a specific gas based upon the oxidizing/reducing nature of the gas. Thus, the methods of the present invention may be utilized to produce a sensor that will be sensitive to a specific gas, even where the specific gas is present in a gaseous mixture to be analyzed.

In general, the methods for selecting a metal oxide with selectivity for a specific gas for use in a sensor involves: determining the reducing or oxidizing nature of a specific gas to classify the nature of the gas; classifying a metal oxide on the basis of its crystal structure; assess the specific gas-metal oxide interactions at the crystal structure's surface; and selecting the metal oxide with the crystal structure possessing a surface most likely to react with the specific gas.

The detection process of oxidizing/reducing gases by semiconducting metal oxides involves the change in the conductivity of the metal oxide in the presence of the gas due to catalytic reduction-oxidation (redox) reactions occurring at the surface of the metal oxides. These catalytic reactions are controlled by the electronic structure of the metal oxide as well as by the chemical composition, crystal structure, and relative orientation of the surfaces of the metal oxide phase(s) exposed to the gas. Metal oxides are polymorphic compounds and thus may exist in various crystalline forms, each of which is stable in a certain pressure-temperature (P-T) field.

In accordance with the present invention, it has been surprisingly discovered that the ability of selective detection of a specific gaseous analyte in the presence of interfering gas mixtures, i.e., sensor selectivity, may be determined by the careful selection of the crystalline polymorph, i.e. specific crystallographic phase, of a stoichiometrically pure metal oxide to be used for sensing. This is due, in large part, to the fact that semiconducting metal oxides show surface sensitivity to redox reactions involving gases.

The local environment of active sites of metal oxides used for gas adsorption, hydrogen extraction, or oxygen addition, and the orientation of the surface containing these active sites, differ for different phases of a given metal oxide, and thus the catalytic behavior of these phases is different.

For example, oxide phases may expose different types of oxygen vacancies at their surfaces; surface oxygen vacancies formed under reduction conditions have an influence on gas adsorption. These vacancies may result in slightly reduced metal oxide surfaces which undergo re-oxidation by gaseous oxygen, which is adsorption based sensing, or they may order and give rise to crystallographic shear structures that accommodate non-stoichiometric metal oxide compositions known as Magneli phases, which is reaction based sensing. The presence of ordered vacancies and crystallographic shear structures thus provides a mechanism for selective oxidation and may be utilized in selecting appropriate metal oxides.

The metal oxides utilized in accordance with the present invention are binary metal oxides that may be classified into three groups according to their crystallographic characteristics. The gases detected by these metal oxides are oxidizing or reducing gases and similarly fall into three categories.

The first group of metal oxides, classified herein as "rutile structured" metal oxides, possess a rutile structure similar to that found in $TiO_2$. The rutile structure is tetragonal, but in some cases it has been described as a distorted hexagonal close packed oxide array with half the octahedral sites occupied by the metal. Alternate rows of octahedral sites are full and empty. The rutile structure is regarded as an ionic structure. Examples of rutile structured metal oxides include $TiO_2$, $SnO_2$, $CrO_2$, $IrO_2$, $\beta$-$MnO_2$, etc.

The second group of metal oxides, classified herein as "rhenium oxide structured" or "ReO$_3$-type" metal oxides, possess a cubic structure akin to that found for rhenium oxide (ReO$_3$), which is closely related to the structure found in perovskite (CaTiO$_3$). The unit cell of the crystal contains metal atoms at the corners with oxygen at the center edges. Metal oxides which form this structure include WO$_3$, β-MoO$_3$, UO$_2$.

The third group of metal oxides, classified herein as "α-MoO$_3$-type" metal oxides have a unique, weakly bonded 2D layered structure. α-MoO$_3$ is a typical representative of this group.

Gases which may be detected in accordance with the present invention may similarly be placed into three categories. Type I gases are nitrogen-lacking reducing gases including, but not limited to, CO, alcohols, and hydrocarbons. Type II gases are nitrogen-containing reducing gases including, but not limited to, NH$_3$ and amines. Finally, Type III gases are oxidizing gases including, but not limited to, O$_2$, NO, NO$_2$ etc.

In accordance with the present invention, it has been surprisingly found that rutile structured metal oxides are selective in their sensitivity to the nitrogen-lacking reducing gases (Type I); the ReO$_3$-type metal oxides are selective in their sensitivity to the oxidizing gases (Type III); and the α-MoO$_3$-type metal oxides are selective in their sensitivity to the nitrogen-containing reducing gases (Type II).

The first step in preparing a sensor with selectivity for a specific gas is determining the reducing or oxidizing nature of the gas being tested, and then selecting a metal oxide for use in a sensor, on the basis of the crystal structure of the metal oxide. This selection is based on analyzing the primary nature of the gas-metal oxide interactions, i.e., chemisorption vs. reaction-based sensing. The next step is to match a specific oxide within a designated group to a specific gas of a certain type.

For rutile structured metal oxide-nitrogen-lacking reducing gas (Type I) interactions, and also for ReO$_3$-type metal oxide-oxidizing gas (Type III) interactions, the adsorption/desorption characteristics of the gas to the surface of the metal oxide are one of the key factors determining sensitivity, selectivity, response and recovery times of the sensor. The metal oxide may be selected on the basis of the reducing/oxidizing properties of these gases in combination with the known crystal structure of the metal oxide.

After initially selecting the metal oxide for the specific gas, the appropriateness of the specific metal oxide crystal in a sensor for the specific gas may be easily determined utilizing techniques known to those skilled in the art. For example, the characteristics of these oxides may be determined by physical adsorption of the specific gas (carried out on a Micromeritics surface area and pore volume analyzer (e.g. ASAP 2020) manufactured by Micromeritics Instrument Corporation, Norcross, Ga., USA)) and evaluated on the basis of the Brunauer-Emmett-Teller (BET) equation. Other chemical analysis techniques that provide chemisorption related information (e.g. Raman spectroscopy conducted on FT/IR optical instrument) may be carried out with the specific gas of interest to determine which oxide behaves optimally in sensing the gas, and under what specific conditions.

For α-MoO$_3$-type metal oxide-nitrogen-containing reducing gas (Type II) interaction, it is the strength of the bond between the metal atom and oxygen on the exposed surface that determines which gas will be sensed with high sensitivity. The electronic structure of the gas to be detected also needs to be considered, especially with respect to the ease of exchanging electrons with the metal oxide surface. The metal oxide may be selected on the basis of the reducing properties of these gases in combination with the known crystal structure of the metal oxide.

Again, after initial selection of a metal oxide for a specific gas, a simple test to determine the suitability of the metal oxide for the specific gas may be conducted, such as by exposing different crystallographic planes of the metal oxide compound to the gas of interest and selecting the optimum configuration. Crystal growth and patterning techniques allow for growing metal oxide along a preferred crystallographic orientation, thus optimizing the configuration of the metal oxide crystals in the sensor.

There are several other factors that may influence the selection of a given metal oxide for selective gas sensing, and these include the (thermal) stability of the sensor at the operating temperature, the structural stability of the chosen metal oxide phase, and the temperature dependence of the sensing process. These variables may be easily accounted for once the proper choice of metal oxide phase has been made. In addition, in accordance with the present invention, multisensor arrays of inherent specificity to different gases may be constructed.

Once chosen, the metal oxide may be formed as a thin film metal oxide and utilized in forming a sensor for the specific gas.

The sensors of the present invention include a substrate material coated with a thin film metal oxide that is highly selective for the permeation of a selected gas with reduced interference from other gases. Electrodes placed between the substrate and the thin film metal oxide detect the presence of a selected gas, permitting the qualification and/or quantification of the selected gas in a sample with little interference from other gases present in the sample.

The thin film metal oxide utilized in the sensor of the present invention is a single un-doped metal oxide component having high specificity to a specific gas, whereas the prior art utilized mixed oxides, which included dopants, to improve the sensitivity of a sensor to a specific gas. Typically, dopants were added to prior art sensors in amounts ranging from at least 1% to 8% by weight of the metal oxide.

The substrate of the present invention may be made of numerous materials including, but not limited to, Si/SiO$_2$, SiC, GaN, etc., but is preferably made of aluminum oxide, Al$_2$O$_3$.

Electrodes are placed on the surface of the substrate, and are then coated with a thin film metal oxide. Electrodes suitable for use with the sensor of the present invention are known to those skilled in the art and include, but are not limited to, gold, silver, tungsten, chromium, titanium, etc. Preferably, gold electrodes are used in the sensor of the present invention.

The electrodes may be provided on the substrate by any suitable method. For example, electrodes may be placed on the surface of the substrate and the thin film metal oxide may then be applied to the electrodes and substrate, thereby coating both and adhering the electrodes to the substrate. Other methods for applying the electrodes to the substrate include, but are not limited to, lithographic techniques, sputtering, laser processing, photochemical methods, etc.

The thin film metal oxide preferably is a substantially pure metal oxide, which does not have a dopant added thereto. Methods for applying the thin film metal oxide are known to those skilled in the art and include, but are not limited to, ion beam deposition, plasma polymerization of appropriate gases, electron beam polymerization of appropriate monomers, chemical or plasma assisted chemical vapor deposition, e-beam, thermal or laser beam evaporation or sputtering of solid dielectric sources, metallic-organic chemical vapor deposition, laser ablation and excimer laser interactions with appropriate gases at the substrate surface.

Prior to providing the substrate with the thin film metal oxide, it may be preferable to clean the surface of the substrate. Satisfactory cleaning can be provided by rinsing the substrate in ethanol, distilled water, prior to mounting the substrate in the vacuum chamber utilized for the ion beam deposition. The surfaces of the substrates may also be cleaned while in the vacuum chamber immediately before initiating the ion beam deposition by bombarding the substrate with a low-energy beam of chlorine ions at a dose of about $1 \times 10^{17}/cm^2$ while the substrate is heated to temperature of about 500° C. This ion beam cleaning procedure is similar to reactive ion etching and provides surfaces which are conducive to good epitaxial growth on the substrate.

A vacuum deposition method such as evaporation, plasma assisted chemical vapor deposition, or a sputtering method may be used for forming the thin film metal oxide. In the sputtering method, predominantly neutral atomic or molecular species are ejected from a target, which may be formed from the material to be deposited, under the bombardment of inert gas positive ions, e.g., argon ions. The high energy species ejected will travel considerable distances to be deposited on the substrate held in a medium vacuum, e.g. $10^{-4}$ to $10^{-2}$ mbar. The positive ions required for bombardment may be generated in a glow discharge where the sputtering target serves as the cathode electrode to the glow discharge system. The negative potential (with respect to ground and the glow discharge) is maintained in the case of insulating target materials by the use of radio frequency power applied to the cathode, which maintains the target surface at a negative potential throughout the process. DC power may be applied when the target is an electrically conducting material. The advantage of such techniques is that control of the target material is greatly enhanced, and the energy of the species ejected is very much higher than with evaporation methods e.g. typically 1 to 10 eV for sputtering as compared with 0.1 to 0.5 eV for evaporation methods.

In magnetron sputtering processes, the plasma is concentrated immediately in front of the cathode (target) by means of a magnetic field. The effect of the magnetic field on the gas discharge is dramatic. In that area of discharge where permanent magnets, usually installed behind the cathode, create a sufficiently strong magnetic field vertically to the electric field, secondary electrons resulting from the sputter bombardment process will be deflected by means of the Lorenz force into circular or helical paths. Thus the density of electrons immediately in front of the cathode as well as the number of ionized argon atoms bombarding the cathode are substantially increased. There is an increase in plasma density and a considerable increase in deposition rate. Bias sputtering (or sputter ion plating) may be employed as a variation of this technique. In this case the substrate is held at a negative potential relative to the chamber and plasma. The bombardment of the substrate by Argon ions results in highly cleaned surfaces. Sputtering of the target material onto the substrate throughout this process results in a simultaneous deposition/cleaning mechanism. This has the advantage that the interfacial bonding is considerably improved. In sputter ion plating systems the substrate is held at a negative potential. In this case the relative potentials are balanced to promote preferential sputtering of the target material. The target voltage will be typically less than 1 kV, dependant on system design and target material. The substrate may be immersed in its own localized plasma dependent upon its bias potential, which will be lower than that of the target. The exact voltage/power relationship achieved at either target or substrate depends upon many variables and will differ in detail from system to system.

The vacuum chambers and ancillary equipment, including micro-processor gas control units and a variety of targets used in these methods, may be purchased commercially. Many variations in design are possible but most employ the use of "box" shaped chambers which can be pumped down to high vacuum for use in any of the vacuum deposition processes mentioned. Systems are normally, but not exclusively, dedicated to one deposition process.

Refinements to the system can, if desired, be employed. For example, the use of an intermediate vacuum station between the air (input side) and the deposition chamber may be employed to generate an Argon ion glow discharge which cleans the substrate surface by ion bombardment prior to its entry into the vacuum deposition chamber and also heats the substrate.

Several heating methods exist, e.g., resistive, inductive, electron beam impingement etc., although the preferred method is an ion beam source where a beam of ions impinge onto the coating material contained in a water-cooled crucible. The use of multi-pot crucibles or twin source guns, enable multiple layers and graded stoichiometry layers to be deposited with the aid of electronic monitoring and control equipment.

In ion-plating, negative bias applied to the substrate in an inert gas promotes simultaneous cleaning/deposition mechanisms for optimizing adhesion as described in the sputtering process. Bias levels of −2 kV are typically used but these can be reduced to suit substrates. As operating pressures are higher in the ion plating technique, e.g. $10^{-3}$ to $10^{-2}$ mbar, gas scattering results in a more even coating distribution. To protect the filament the electron beam gun in the ion plating technique is differentially pumped to maintain vacuum higher than $10^{-4}$ mbar.

In the plasma assisted chemical vapor deposition (PACVD) method, the substrate to be coated is immersed in a low pressure (0.1 to 10 Torr) plasma of the appropriate gases/volatile compounds. This pressure may be maintained by balancing the total gas flow-rate against the throughput of the pumping system. The plasma may be electrically activated and sustained by coupling the energy from a power generator through a matching network into the gas medium. Thin films have been successfully deposited from direct current and higher frequency plasmas well into the microwave range. At high frequencies the energy may be capacitatively or inductively coupled depending on chamber design and electrode configuration. Typically a 13.56 MHz radio-frequency generator would be used having a rating which would allow a power density of between about 0.1 $W/cm^2$ and about 10 $W/cm^2$ in a capacitatively coupled parallel-plate type reactor. The substrate, which could be set at a temperature of up to 400° C., may be grounded, floating or subjected to a dc voltage bias as required. Typical deposition rates for this technique can be favorably compared with those obtained by sputtering. The deposition of the thin film metal oxide may be achieved by immersing a substrate in a plasma containing a metal compound, such as molybdenum or tungsten, and oxygen under appropriate processing conditions.

Preferably, an ion beam deposition process is used to coat the substrate. In an ion beam deposition process, a radio frequency (RF) (13.56 MHz) powered inductively-coupled ion source generates hydrocarbon ions which are then deposited on the surface of substrate. Good deposition results have been accomplished using the following parameters: RF power 179 watts; gas flow for $CH_4/H_2$ of 13.6 sccm/20 sccm; an ion energy of 300 eV; a substrate temperature of 100° C.; and a pressure of $10^{-4}$ Torr. The deposition conditions may be monitored with a mass analyzer and the thickness of the thin film metal oxide may be controlled by adjusting the beam flux.

The ion beam may be maintained at a relatively low energy level so as to inhibit losses by sputtering and to prevent the penetration of the ions into the substrate beyond a distance of only a few monolayers. As the metal ions from the ion beam initially accumulate in the near-surface region of the substrate as a continuous thin metal film, any metal oxide formation present within the substrate at a temperature in the range of from about room temperature to about 300° C. would most likely occur at the film-substrate interface due to the finite range of the ions.

The ion beam energies utilized in practicing the present invention may range from about 10 to about 1000 eV with current densities in the range of about 1 to about 10 microamps/$cm^2$. The ion beams within this energy range are sufficient for forming thin film metal oxides having a thickness in the range of from about 5 nm to about 500 nm, more preferably from about 50 nm to about 200 nm. The use of these relatively low ion beam energies is sufficient to effect the athermal formation of a thin film metal oxide on the surface of the substrate and any previously formed portion of the thin film metal oxide layer without causing undesirable ion implantation below the near surface regions of the substrate.

More preferably, the thin oxide layer is applied to the substrate by a dual ion beam deposition system. Ion-beam sputtering from a metal target may be conducted utilizing filamentless radio-frequency inductively coupled plasma (RFICP) primary source, with the film partially oxidized during growth using an RFICP assist source directed at the substrate. Preferably, oxygen may be provided in secondary plasma, so that a thin film metal oxide is formed on the substrate.

The ion beam deposition may be carried out in a suitable chamber or deposition chamber evacuated to a pressure in the range of about $1\times10^{-7}$ to about $1\times10^{-10}$ torr. The ion beam deposition and the heating of the substrate is maintained until the film reaches the desired thickness. Normally, with ion beam energies in the aforementioned range a film growth rate in the order of about 1 nm/min is provided. With such a growth rate a reaction duration of about 1 minute to about 5 hours would be required for forming a film with a thickness in the range of about 5 nm to about 500 nm, more preferably from about 50 nm to about 200 nm.

In addition, suitable thin film metal oxides may be formed by a sol-gel deposition method, a plasma ashing method, or a solution coating method.

The sol-gel process involves the hydrolysis and polycondensation of a metal alkoxide and an alcohol to produce an inorganic oxide gel which is converted to an inorganic oxide glass by a low temperature heat treatment. The metal alkoxides, e.g., alkoxides of molybdenum or tungsten such as molybdenum isopropoxide or tungsten isopropoxide, may be used in combination with an alcohol, such as n-butanol, to form the metal trioxide, i.e., molybdenum trioxide or tungsten trioxide, respectively. Because these isopropoxides are reactive to atmosphere, they may be mixed in an enclosed container under a nitrogen atmosphere. The resulting sol is allowed to age and settle, and the sol may then be deposited on a substrate and spun at about 1000 rpm to about 5000 rpm, with a range of about 2000 rpm to about 3000 rpm being preferred, for a period of time ranging from about 2 seconds to about 60 seconds, with a range of about 25 seconds to about 45 seconds being preferred. The spinning may be repeated about 5 to about 15 times, with heating to a temperature of about 50° C. to about 100° C., preferably about 65° C. to about 85° C. for a time ranging from about 5 to about 30 minutes, more preferably, from about 10 to about 20 minutes.

The gel coated substrate then undergoes suitable drying and firing stages to convert the coating into an inorganic oxide glass. The precise conditions with respect to temperature and residence time in the various stages of conversion are dependent upon the gel composition and its tolerance to relatively rapid changes in its environment. Porosity and integrity of the coating can be significantly affected by these stages. A suitable conversion process would include drawing the gel coated substrate through drying ovens in which the temperature is controlled at approximately 80° C. and subsequently through progressive heat treatment stages which expose the gel coated substrate for a few minutes to temperatures of about 300° C. to about 500° C. The required exposure times are dependent upon the initial thickness of the gel coating, but the drying process should be preferably carried out as slowly as practical. It may be desirable to In some cases, it may be desirable to further treat the thin film metal oxide to ensure the oxidation of any metal utilized in forming the thin film metal oxide. Such further treatments include, but are not limited to, re-oxidizing the film in a sufficient concentration of oxygen, such as 10% $O_2$, or applying an oxidizer such as hydrogen peroxide.

Sensors in accordance with the present invention may be utilized in numerous applications including, but not limited to, automotive on-board diagnostic systems and biosensors. The sensors in accordance with the present invention are resistive gas detectors that rapidly detect, within seconds, very low concentrations of the selected gas, e.g., ammonia or nitrogen dioxide, with reduced interference from other gases. The concentrations of the selected gases that may be detected in accordance with the present invention may be less than about 3 ppm, and may range from about 0.1 ppm to about 1000 ppm. The sensors may, in some embodiments, also include a temperature sensing means such as microheaters, microhotplates, etc.

In accordance with the present invention, it has been surprisingly discovered that for undoped metal oxides, the oxide polymorph used for gas sensing is extremely important. Thus, it has been determined that nitrogen-containing reducing gases, e.g. ammonia and amines, may be best sensed by "loosely bound" layered oxide structures, such as the orthorhombic $\alpha$-$MoO_3$ phase, that enable the reaction of lattice oxygen with the gas and provide easy mechanisms for accommodating the off-stoichiometric M:O ratio. On the other hand, oxidizing gases, such as $NO_2$, destroy oxygen defects and may be easily adsorbed on $ReO_3$-type crystals. Finally, nitrogen-lacking reducing gases, e.g. CO and hydrocarbons, typically react with adsorbed oxygen from the environment and may be sensed by rutile-type structures, such as the polymorphs of $SnO_2$ and $TiO_2$.

In one preferred embodiment, the alpha phase of molybdenum trioxide ($\alpha$-$MoO_3$) is used as the thin film metal oxide in a sensor for detection of ammonia. Excellent sensitivity to ammonia was obtained when the orthorhombic $\alpha$-$MoO_3$ phase was used for sensing, while its other polymorphs have variable sensing properties. The presence of more than one $MoO_3$ polymorph in the thin film metal oxide, i.e., both $\alpha$- and $\beta$-polymorphs, results in an alteration of the selectivity of the film, i.e., an n to p-type conversion of the sensing response and reduced sensitivity to ammonia.

Figure 19:
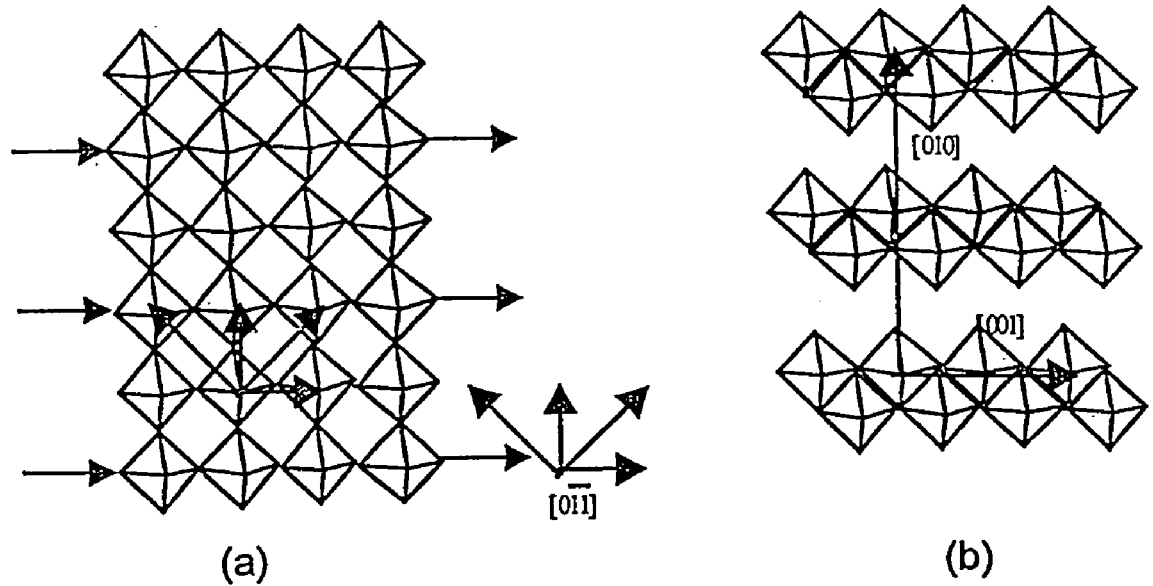
FIG. 19 are diagrams of the structures of $\beta$-$MoO_3$ (FIG. 19(a)) and $\alpha$-$MoO_3$ (FIG. 19(b)).

The $\alpha$-MoO$_3$ polymorph has a layered orthorhombic structure and favors the formation of crystallographic shear planes. Orthorhombic MoO$_3$ crystallizes in a unique 2D layered structure that is built up of double chains of edge-sharing [MoO$_6$] octahedral connected through vertices. In contrast, the $\beta$-phase (monoclinic) of MoO$_3$ has a ReO$_3$-type structure (see FIG. 19; Carcia et al., "Synthesis and Properties of Thin-Film Polymorphs of Molybdenum Trioxide", Thin Solid Films, 155(1): pp. 53–63, (1987)), and is more suited to detecting oxidizing gases. The ReO$_3$-type structure does not contain the Van der Waals gap of the $\alpha$-MoO$_3$. Therefore, $\alpha$-MoO$_3$ upon reduction in catalysis forms the Mo$_{18}$O$_{52}$ structure instead of the ReO$_3$-type Mo$_8$O$_{23}$ shear structure.

The $\alpha$-MoO$_3$ phase has been determined to be selective to ammonia and highly sensitive to amines (which are moderate bases) and the sensing mechanism is consistent with the reduction of MoO$_3$ and the formation of ordered phases, which suggests reaction-based sensing process. On the other hand, the ReO$_3$-type structure of $\beta$-MoO$_3$ was found to be selective to NO$_2$. While not wishing to be bound by any theory, an adsorption (chemisorption) based sensing mechanism may be active in the case of $\beta$-MoO$_3$, which does not affect the bonds in the metal oxide surface, while the lattice oxygen may play a key role in the sensing behavior of $\alpha$-MoO$_3$.

In another embodiment, tungsten trioxide (WO$_3$) is used as the thin film metal oxide in a sensor for the detection of nitrogen dioxide. The crystal structure of WO$_3$ is a distortion of rhenium oxide cubic structure in which tungsten atoms are located in cube corners and the oxygen atoms are located on the cube edges. The distorted structure is stable in several forms giving rise to different phases depending on the temperature. The orthorhombic polymorph of tungsten trioxide was stabilized and was found to have demonstrated specificity for nitrogen dioxide in the presence of interfering gases such as NH$_3$.

Since a given crystal structure may be sensitive to more than one gas, sensing tests at different temperatures may be carried out to identify the optimum operating temperature for the specific sensor so the sensor remains within the phase stability field of the particular polymorph of the oxide. Phase stability depends on the grain/particle size of the sensing element (oxide crystal), the operating temperature and pressure conditions, and the presence of impurities.

With respect to biosensors, a urea microsensor may be prepared by incorporating urease in MoO$_3$ sol-gel matrices. Urease may be incorporated into the sol-gel matrix by methods know to those skilled in the art. In one embodiment, a first thin film metal oxide coating may be applied to a substrate and electrodes, urease may be then applied by dropping it onto the coated sensor, and a second thin film metal oxide coating may then be applied.

Figure 20:
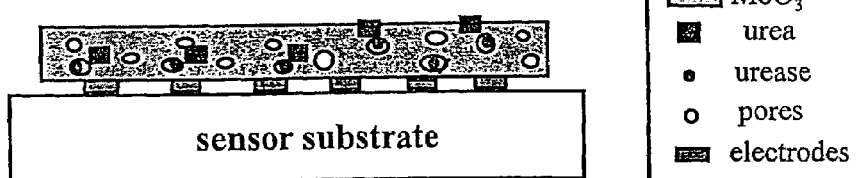
FIG. 20 is a diagram depicting a biosensor in accordance with the present invention.

As gaseous ammonia is produced by the reaction of urease with urea, this system may measure the concentration of ammonia, which correlates with the urea concentration levels in the sample tested. FIG. 20 provides a schematic representation of this urea microsensor. The biological component, the enzyme urease, may be replaced with any other enzyme, cell, antibody, etc. that preferentially reacts with a pathogen releasing gaseous ammonia or amines, thereby permitting the production of a selective biosensor to ammonia or amine suitable for the diagnosis of a specific condition.

In operation, the sensors of the present invention operate in a similar fashion. First, a gas or gaseous mixture is contacted with the thin film metal oxide. Conductors are provided to connect the electrodes of the sensor to electrical measuring means for measuring the resistance and/or capacitance, and/or impedance of the thin film metal oxide. The resistance and/or conductance, and/or impedance is measured by the electrical measuring means. Changes in the composition of the gas or gaseous mixture which result in a change of resistance and/or conductance, and/or capacitance, and/or impedance are observed as changes in the resistance and/or conductance, and/or capacitance and/or impedance recorded by the measuring means.

In operation, the first electrode and second electrode are connected by conductors to an electrical measuring means for measuring the resistance and/or capacitance, and/or impedance of the thin film metal oxide and the sensor is contacted with a gas or gaseous mixture. The resistance and/or capacitance, and/or impedance is measured by the electrical measuring means and changes in the composition of the gas or gaseous mixture which result in a change of resistance and/or capacitance, and/or impedance are observed as changes in the resistance and/or capacitance, and/or impedance recorded by the electrical measuring means.

The resistance and/or conductance, and/or impedance may be measured directly. Alternatively, the measurement may be carried out indirectly by incorporating the sensor in a feedback circuit of an oscillator such that the oscillator frequency varies with composition of the gas or gaseous mixture. Gas composition may then be determined using an electronic counter. The signal thus produced may be used to modulate a radio signal and thereby be transmitted over a distance (e.g. by telemetry or as a pulse train along an optical fiber).

Preferably, the thin film metal oxide has sufficient porosity to give a satisfactory surface area for contact with the gas or gaseous mixture sampled.

The sensors in accordance with the present invention may be utilized in any environment or for any application where the detection of a specific gas, e.g., ammonia or nitrogen dioxide, is required. As noted above, the sensors may be used in both the qualification and quantification of a specific gas in a gaseous mixture sample. The sensors may be especially beneficial for use in automotive processes, such as those involving SCR, and biosensors.

EXAMPLES

The following examples are provided to exemplify, but not limit, the sensors of the present invention.

Example 1

Thin films of molybdenum trioxide were reactively sputter-deposited onto alumina substrates in a dual ion beam deposition system. Ion-beam sputtering from a 12" diameter molybdenum target (CERAC 99.9%) was accomplished using a filamentless radio-frequency inductively coupled plasma (RFICP) primary source (Veeco Instruments Inc., Woodbury, N.Y.), with the film partially oxidized during growth using a RFICP assist source (Veeco Instruments Inc., Woodbury, N.Y.) directed at the substrate. The ratio of oxygen to argon in the secondary plasma was maintained at 1:1 and the overall process pressure was $1.6 \times 10^{-4}$ Torr. The alumina substrates were pre-patterned with 200-micron linewidth interdigitated Au electrodes. Approximately 150-nm MoO$_3$ was deposited over the alumina and Au electrodes. Following deposition, the films were annealed at 500° C. in air for one hour to complete the oxidation to MoO$_3$. The microstructure for some films was examined using a Philips CM12 transmission electron microscope (Philips Electronics, NV) with a LaB$_6$ cathode and an incident energy of electrons of 120 keV, and a LEO-1550 Field Emission Gun Scanning Electron Microscope (Leo Electron Microscopy, Cambridge, UK). The films were found to have the orthorhombic phase of MoO$_3$.

The DC electrical conductivity was measured on a gas flow bench using a two-point technique. Typically 1V was applied across the sample and the current measured using a Keithley 6517A electrometer (Keithley Instruments, Inc., Cleveland, Ohio). The sample was mounted in a 1" diameter quartz tube and was externally heated with a tube furnace. A thermocouple was typically placed in the vicinity of the specimen. The sensor resistance was measured over the temperature range 250° C.–565° C.±5° C. in the presence of up to 500 ppm of NH$_3$, NO, NO$_2$, C$_3$H$_6$, CO and H$_2$. The measurements were done in 10% accompanying O$_2$ unless otherwise indicated, with the balance of the gas N$_2$. The total flow rate was typically 2 liters/minute. The influence of water vapor was examined by mixing the gas mixture with a N$_2$ gas stream that was bubbled through water. The resulting water concentration was about 1%.

Figure 2:
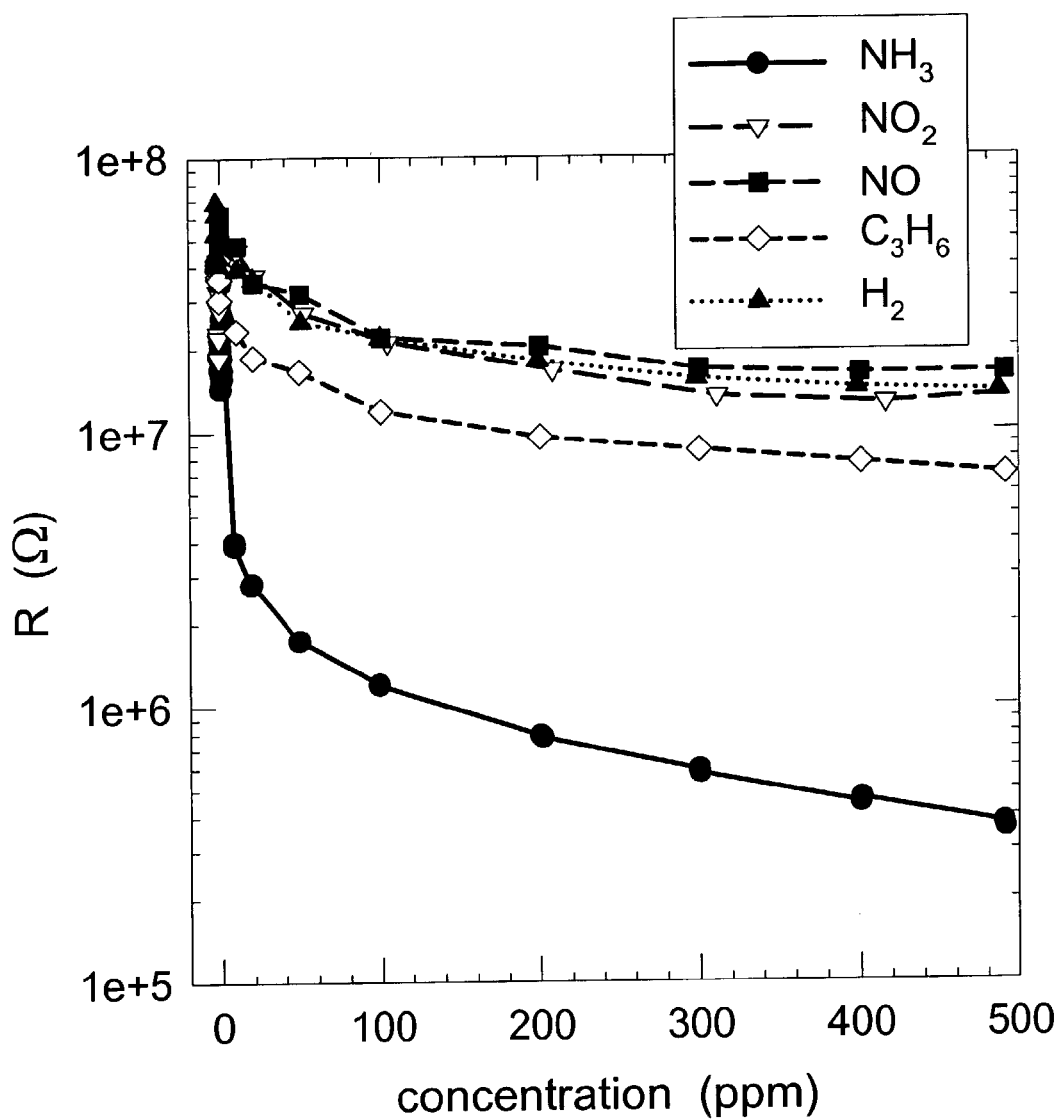
FIG. 2 is a graph comparing the resistance of a $MoO_3$ film at 438° C. as a function of concentrations of $NH_3$, $NO_2$, $NO$, $C_3H_6$ and $H_2$. The accompanying $O_2$ concentration was 10%. Plotted are the resistance values at the end of each 10 minute pulse.

FIG. 1 shows the variation in resistance with time for a MoO$_3$ film at 438° C. Shown are data for separate sequences of NH$_3$ and C$_3$H$_6$ gas pulses. The concentrations of the 10 minute pulses were the same for both gases and were stepped down from 490 ppm to 10 ppm. Each pulse was separated by a 10 minute interval of 0 ppm concentration. The accompanying oxygen concentration was 10%, with the balance of the gas N$_2$. A large response to NH$_3$ was observed, with the 10 ppm pulse easily discernible and having a resistance value lower than that measured in 490 ppm C$_3$H$_6$. The resistance in 490 ppm NH$_3$ was only about $\frac{1}{17}^{th}$ of that observed for an equal amount of C$_3$H$_6$. FIG. 2 further demonstrates the relative selectivity of the ammonia response, comparing the resistance change at 438° C. as a function of concentrations of NH$_3$, NO$_2$, NO, C$_3$H$_6$ and H$_2$. Plotted are the resistance values at the end of each 10 minute pulse. The MoO$_3$ film was very sensitive to concentrations of NH$_3$ at this temperature and the selectivity of the NH$_3$ response was greater than the NO$_2$ and H$_2$ responses.

Figure 3:
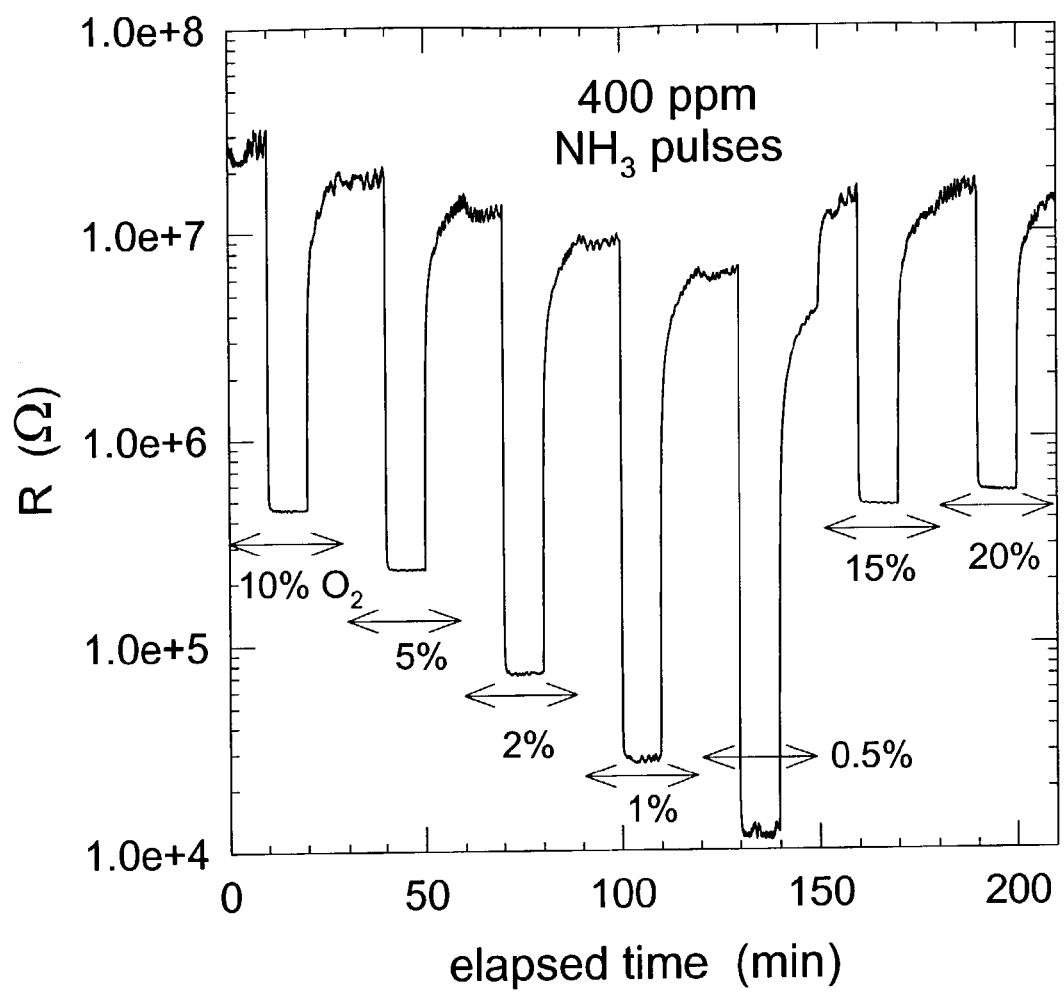
FIG. 3 is a graph comparing the response of a $MoO_3$ at 438° C. to a 10 minute, 400 ppm $NH_3$ pulse for several values of the accompanying $O_2$ ranging from 0.5% to 20%.
Figure 4:
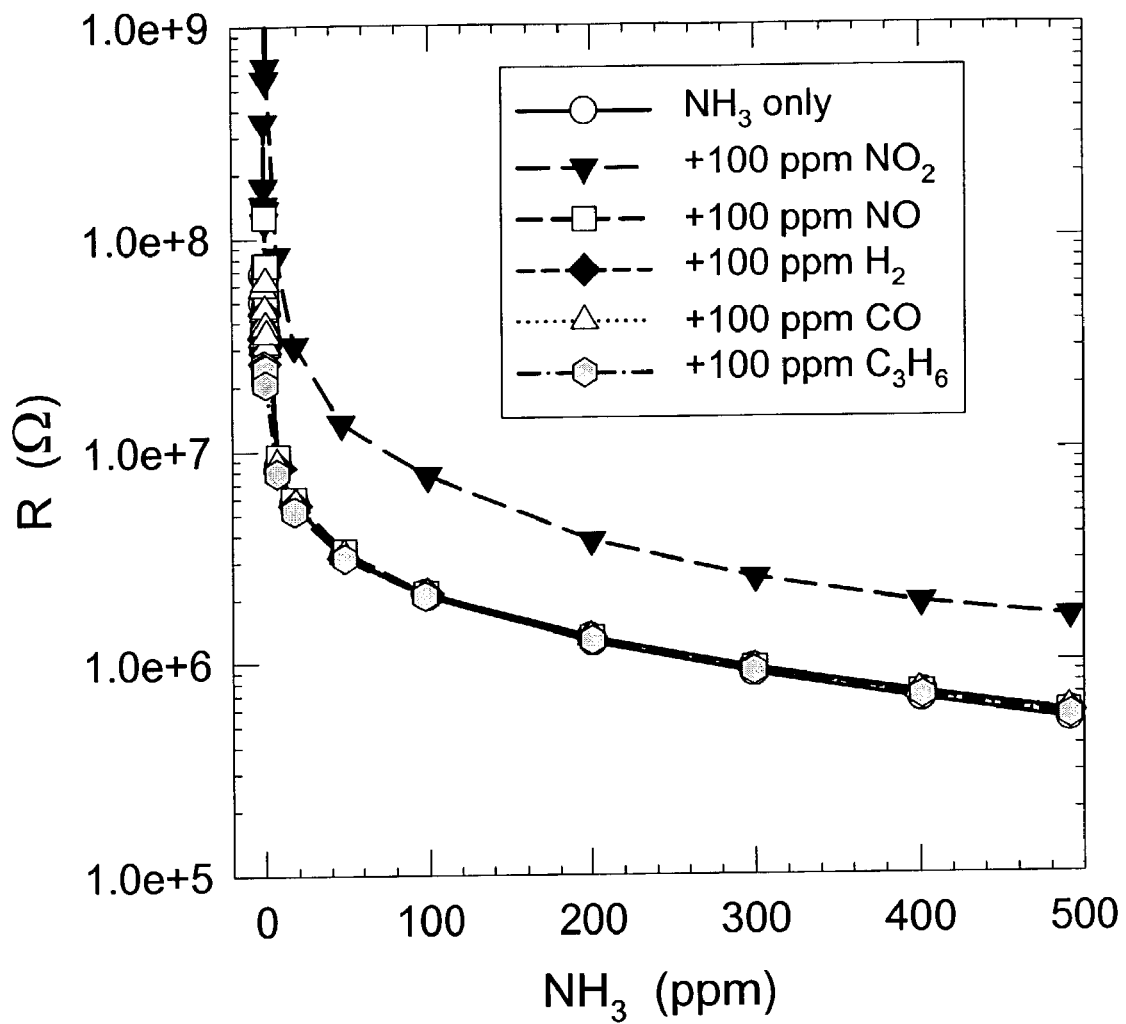
FIG. 4 is a graph depicting the cross-sensitivity of the $NH_3$ response at 440° C. to 100 ppm concentrations of accompanying $NO_2$, NO, $H_2$, CO and $C_3H_6$. The accompanying $O_2$ concentration was 10%.
Figure 5:
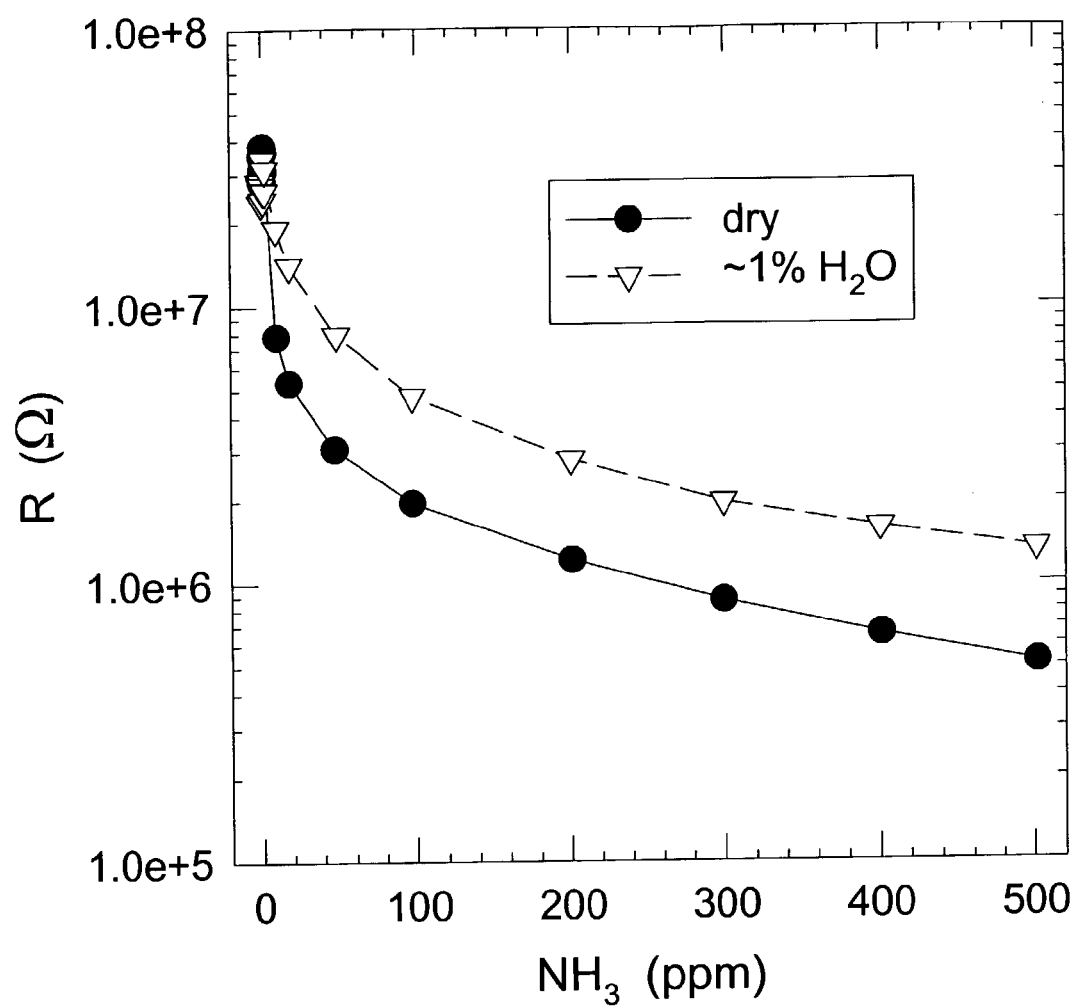
FIG. 5 is a graph depicting the variation in resistance of a $MoO_3$ film in a dry state and with about 1% water at 440° C. and in 10% $O_2$ as a function of the $NH_3$ concentration.

FIGS. 3, 4 and 5 demonstrate the cross-sensitivity of the ammonia response to accompanying levels of O$_2$, NO$_2$ and H$_2$O respectively. FIG. 3 shows the decreases in resistance at 438° C. as a function of time for 10 minute, 400 ppm NH$_3$ pulses with accompanying O$_2$ concentrations ranging from 0.5% to 20%. The NH$_3$ sensitivity was greatly affected by the accompanying O$_2$, with the 400 ppm NH$_3$ pulse decreasing the resistance to ~12 kΩ in 0.5% O$_2$ compared to only ~540 kΩ in 20% O$_2$. This cross-sensitivity was most pronounced for O$_2$ in the range 0.5% to 5%. Varying the accompanying amounts of O$_2$ in the range of 10% to 20% resulted in only small changes of the NH$_3$ sensitivity. FIG. 4 summarizes the cross-sensitivity of the NH$_3$ response at 440° C. to 100 ppm concentrations of accompanying NO$_2$, NO, H$_2$, CO and C$_3$H$_6$. The accompanying O$_2$ was 10% and plotted are the resistance values at the end of each 10 minute gas pulse. For NH$_3$ concentrations 10 ppm and above the response was relatively unaffected by 100 ppm concentrations of accompanying NO, H$_2$, CO and C$_3$H$_6$. However, the NH$_3$ sensitivity was lessened by the accompanying NO$_2$. In 490 ppm NH$_3$ the resistance decreased to ~0.6MΩ, compared to only ~1.6MΩ in the additional presence of 100 ppm NO$_2$.

Accompanying H$_2$O vapor also lessened the NH$_3$ sensitivity. Compared in FIG. 5 were the responses to NH$_3$ at 440° C. for the cases of 0% and ~1% accompanying water. In 490 ppm NH$_3$, the resistance when exposed to 1% H$_2$O was more than twice the value when dry.

Figure 6:
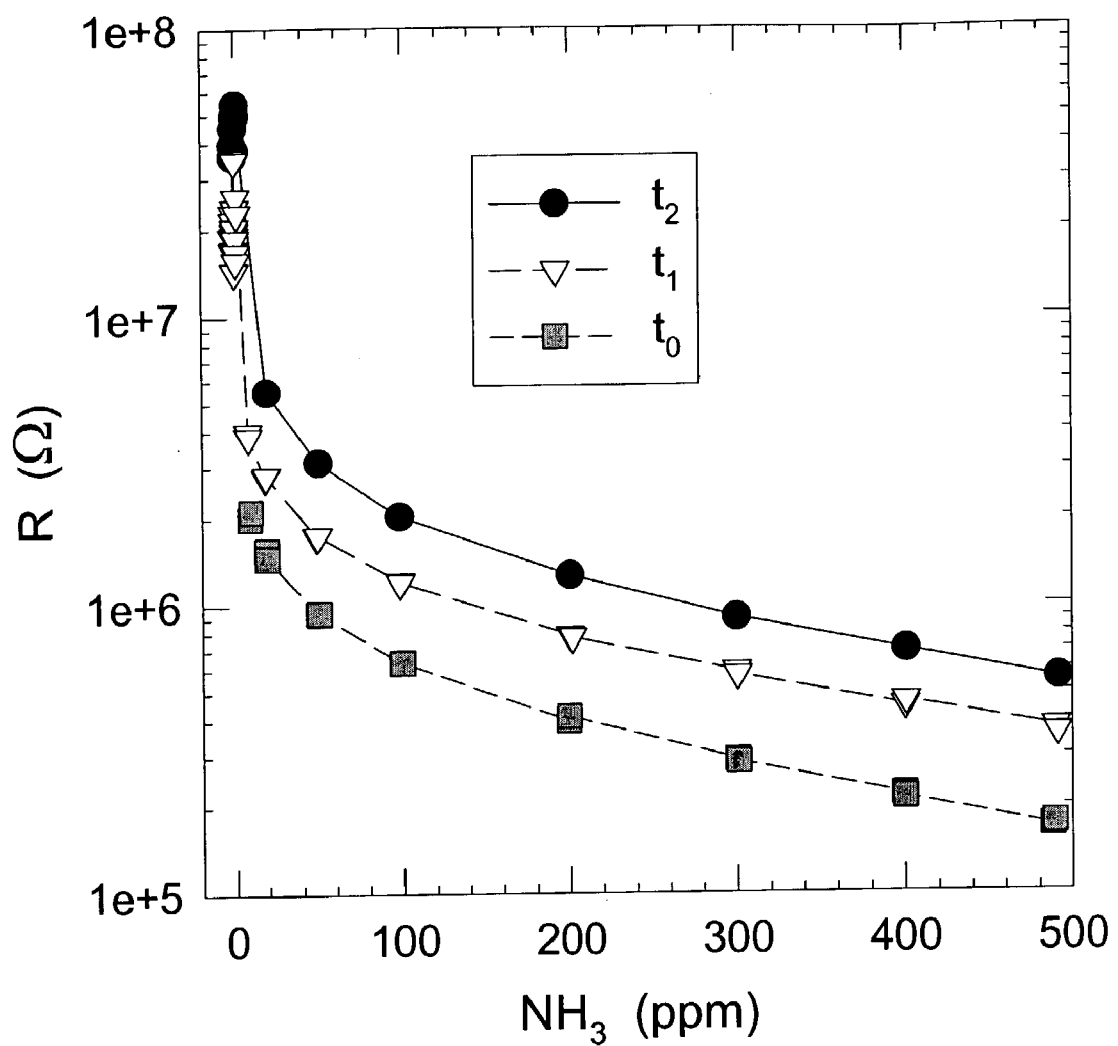
FIG. 6 is a graph demonstrating the variation in resistance of a $MoO_3$ film as a function of $NH_3$ concentration at elevated temperatures ($t_2 > t_1 > t_0$) over time.

FIG. 6 shows the NH$_3$ response of a film at three different times. Several measurements were made between each set, with each lasting typically over ten hours. Microscopic examination of one of the films measured for an extended time revealed microstructural changes. For this aged film the MoO$_3$ was missing on the Au electrode near its edge. In addition, the MoO$_3$ film on the alumina exhibited a finer structure with greater porosity compared to the film in its as-deposited state. These changes may be due to diffusion processes or evaporation of the film.

Figure 7:
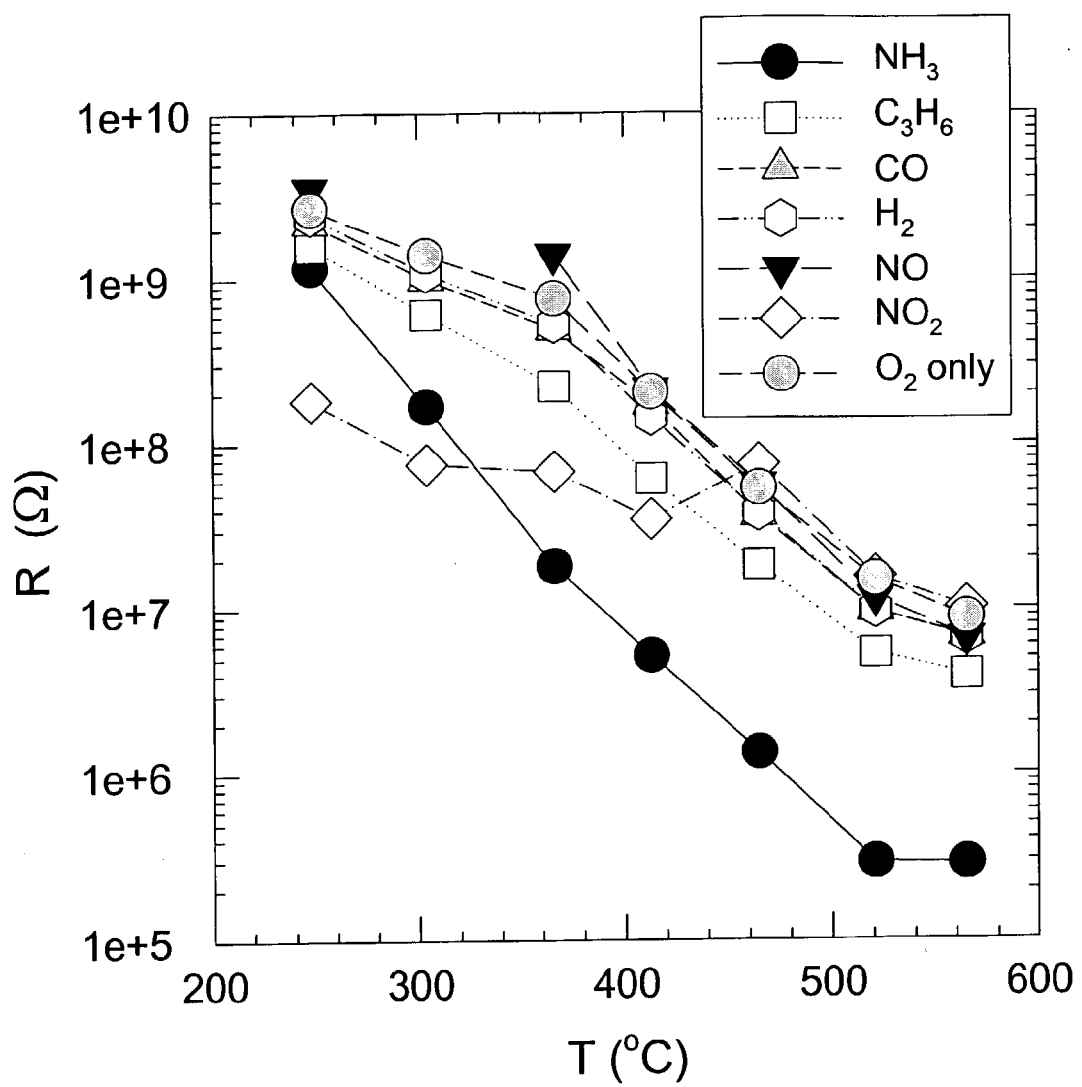
FIG. 7 is a graph demonstrating the resistance variation as a function of temperature for a $MoO_3$ film exposed to 400 ppm of $NH_3$, $C_3H_6$, CO, $H_2$, NO and $NO_2$ in 10% $O_2$.

The temperature dependences of the gas responses are summarized in FIG. 7. Plotted are the resistance values as a function of temperature in the range 250° C.–565° C. for a MoO$_3$ film exposed to 400 ppm of NH$_3$, C$_3$H$_6$, CO, H$_2$, NO and NO$_2$ in 10% O$_2$. The relative NH$_3$ selectivity decreased below 400° C.

Example 2

The surface of one MoO$_3$ film prepared in accordance with Example 1 was examined several times by x-ray photoelectron spectroscopy (XPS). Each set of measurements was taken after the film was exposed to a different gas. The film was placed in a quartz tube (1" diameter and 24" length) and treated by heating in a furnace at ~465° C. in a flowing atmosphere for 30 minutes, and then allowed to cool in the same gas stream by pulling the quartz tube containing the specimen out of the furnace. After the film cooled it was transferred to the XPS system and placed under vacuum. The transfer process typically took at least five minutes, during which the film was exposed to air. Some oxidation of the film may have occurred during this time. After measurement, the process was repeated for other gas compositions. All XPS analyses were performed on a Kratos Axis-165 spectrometer, manufactured by Kratos Analytical (Chestnut Ridge, N.Y.). The X-ray source provided monochromatic Al K$_\alpha$ radiation (1486.6 eV) and was operated at 300 W. For all acquisitions the area irradiated by the X-ray beam was about 1000 μm in diameter. Following each treatment, three sets of measurements from areas equally distributed across the sensor were acquired to check for reproducibility.

The analyzer was operated at an 80 eV pass energy for all survey spectra and 20 eV pass energy for the acquisition of all core level spectra. A low energy electron charge neutralizer was utilized to minimize charging effects. The system base pressure was typically 1×10$^{-9}$ Torr during all analyses. The data system and software routines used were supplied by the instrument manufacturer. Atomic concentrations were obtained by integration of the core level spectra, with appropriate corrections made for photoionization cross-sections and instrument transmission function. High-resolution core level spectra were fitted using a least-squares fitting routine to determine core level binding energy positions. Appropriate software routines from the manufacturer were used to assure a consistent estimate of the background.

Figure 8:
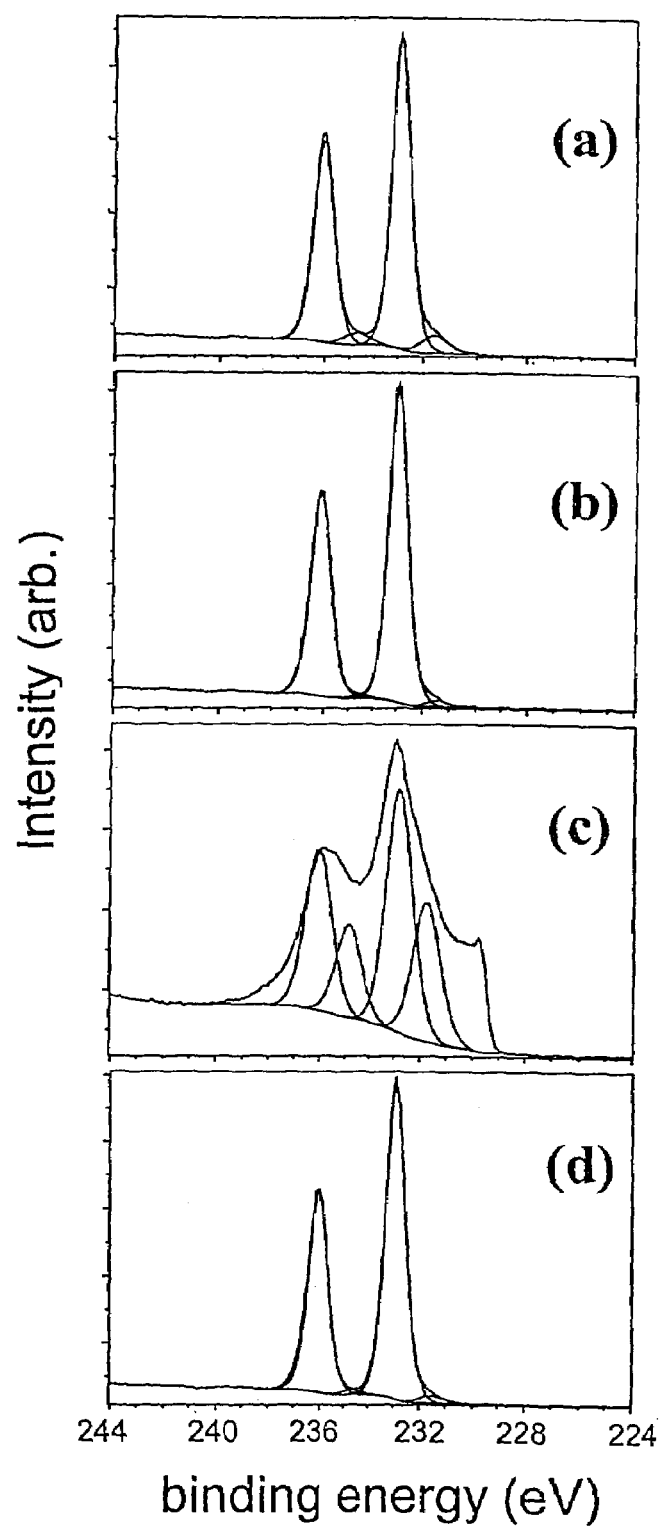
FIG. 8 are x-ray photoelectron spectroscopy (XPS) spectra obtained from the same $MoO_3$ films after exposure to different gas environments at ~465° C.

The XPS results in FIGS. 8a–d show the Mo (3d) peak of MoO$_3$ spectra after exposure to different atmospheres at ~465° C. The sequence of the measurements was in the order they were given, with FIG. 8a measured first. FIG. 8a shows the Mo (3d) spectra after exposure to 1000 ppm $NH_3$ in 10% $O_2$. FIG. 8b gives the spectra for 10% $O_2$ only, FIG. 8c for 1000 ppm $NH_3$ in 0.5% $O_2$, and finally FIG. 8d for 1000 ppm $C_3H_6$ in 10% $O_2$ (this spectra was taken after re-oxidizing the film in 10% $O_2$). The main Mo 3d peaks evident in FIG. 8b at ~232.9 eV and ~236.1 eV were consistent with $Mo^{+6}$ (i.e., fully oxidized $MoO_3$). Note that in FIG. 8a, for the case of 1000 ppm $NH_3$ in 10% $O_2$, these peaks exhibit a small "shoulder" at lower binding energies. This is consistent with a small amount of the surface Mo being reduced to a lower oxidation state, lowering from $Mo^{+6}$ to one in the range of $Mo^{+5}$ to $Mo^{+4}$. It is estimated from a deconvolution of the spectra in FIG. 8a that about 93% of the surface Mo remained as $Mo^{+6}$. By comparison, in FIG. 8b the $Mo^{+6}$ fraction was over 98%. In FIG. 8c, for the case of 1000 ppm $NH_3$ in 0.5% $O_2$, the reduction of the surface Mo was substantial. In this environment the film changed from a transparent appearance to a black and opaque. It is estimated that only about 30% of the surface Mo remained as $Mo^{+6}$, with the rest in the range of $Mo^{+5}$ to $Mo^{+4}$. After re-oxidizing the film in 10% $O_2$, most of the film surface returned to $Mo^{+6}$, which was verified by XPS, exposure to 1000 ppm $C_3H_6$ in 10% $O_2$ resulted in only a slight reduction of the Mo. The Mo oxidation states as determined by XPS are summarized for the different gas exposures in Table 1.

TABLE 1

Summary of the XPS data for a $MoO_3$ film

| Gas | % $Mo^{+6}$ | % ($Mo^{+5}$ to $Mo^{+4}$) |
|---|---|---|
| 1000 ppm $NH_3$ in 10% $O_2$ | 92.6 | 7.4 |
| 10% $O_2$ only | 98.2 | 1.8 |
| 1000 ppm $NH_3$ in 0.5% $O_2$ | 30.1 | — |
| 1000 ppm $C_3H_6$ in 10% $O_2$ | 97.6 | 2.4 |

Measurements on a similar film at 468° C. demonstrated that 1000 ppm $NH_3$ decreased the resistance by more than $10^2$ in 10% $O_2$ and by more than 103 in 0.5% $O_2$. Although the resistance in 1000 ppm $C_3H_6$ was not measured, FIGS. 1 and 2 demonstrate a reduced sensitivity to $C_3H_6$ relative to that for $NH_3$. Comparing the XPS and resistance measurements, a qualitative correlation was found between the reduction of the oxidation state of the surface Mo and the reduction in resistance upon gas exposure.

The films were found to be very sensitive to $NH_3$ above 400° C., and relatively selective when compared to the responses to NO, $NO_2$, $C_3H_6$, CO and $H_2$. The $NH_3$ sensitivity, however, decreased in the presence of accompanying levels of $O_2$, $NO_2$ and $H_2O$. The resistance of the $MoO_3$ films was found to be slowly increasing with time. Microstructural changes were observed in an aged film. These changes may be due to diffusion processes or evaporation of the film. XPS measurements on films exposed to different atmospheres show that the decreased resistance measured in the presence of ammonia was also accompanied by a partial reduction of the $MoO_3$ on the surface. Exposure to $C_3H_6$ resulted in only a slight reduction of the surface $MoO_3$, consistent with reduced gas-sensitivity relative to that for $NH_3$.

Example 3

Molybdenum trioxide thin films were prepared for use as gas sensing elements. One set of films was sputter-deposited onto alumina substrates-containing gold interdigitated electrodes on them in a dual ion beam deposition chamber from a molybdenum target (CERAC, 99.9%, 12" diameter) and oxygen in secondary plasma. The deposition system consisted of a filamentless Radio-Frequency Inductively Coupled Plasma (RFICP) primary source and a RFICP assist source (Veeco Instruments Inc., Woodbury, N.Y.) directed at the substrate. The process pressure was $2.13 \times 10^{-2}$ Pa. The ratio of oxygen to argon in the secondary plasma was maintained at 5:5 (sccm). The target was water-cooled to room temperature and was mounted at 45 degrees with respect to the primary source. The sample stage could be rotated continuously (2 rpm) or tilted from 0–75 degrees with respect to the target normal and was also water-cooled. The distance from the primary source to the target, the assist source to the sample stage, and the target to the sample were 356 mm, 508 mm and 381 mm respectively. The substrate was positioned such that its normal maintained an angle of 30° to the incident flux of atoms. The substrate was kept rotating during deposition to attain better uniformity.

Example 4

Sol-gel processing was used to form thin molybdenum trioxide films. Precursors for $MoO_3$ were prepared by mixing molybdenum isopropoxide and n-butanol to make 0.1M solutions. Since molybdenum isopropoxide is reactive to atmosphere, the mixing was done inside a glove box under nitrogen atmosphere. After mixing, the sol was mechanically agitated for 5 minutes inside the glove box and then sealed airtight. Ultrasonic agitation was then performed for 2 hours and the sol was allowed to age and settle. A black opaque liquid was obtained after 24 hours of aging. The sol was dropped on the sensor substrates and spun at 2500 rpm for 30 seconds in a spin coater (Chemat Technology, KW-4A from Chemat Technology, Inc., Northridge, Calif.). In order to obtain films of comparable thickness to that obtained by ion beam deposition, the spinning was repeated 10 times with baking at 75° C. between spins for 15 minutes.

Example 5

Transmission electron microscope (TEM) investigations were performed on the films produced in Examples 3 and 4 using a Philips CM12 transmission electron microscope (Philips Electronics, Nev.) with $LaB_6$ cathode and an incident energy of electrons of 120 keV. The ion beam deposited films were analyzed both before and after a stabilization heat treatment of 8 hours at 500° C. The sol-gel films were also characterized before and after a stabilization heat treatment at two different time intervals of 1 hour and 8 hours at 500° C.

Scanning electron microscope (SEM) studies were carried out on a LEO-1550 Field Emission Gun Scanning Electron Microscope (Leo Electron Microscopy, Cambridge, UK) in order to compare the morphology of the films obtained by the two techniques of Examples 3 and 4. Secondary electron imaging was used. All the films were observed directly (without any special specimen preparation techniques) following the sensing tests.

Figure 9:
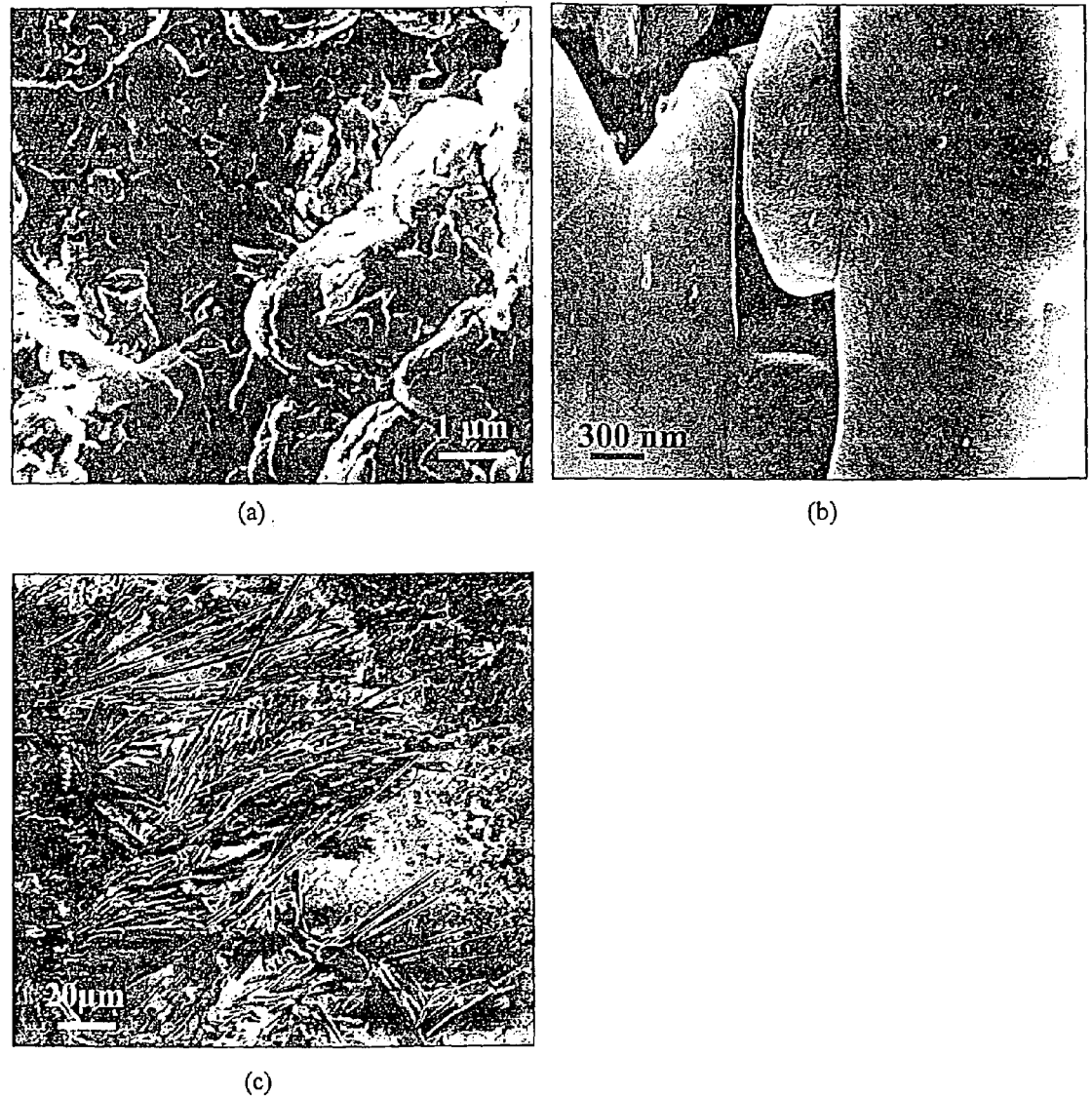
FIG. 9 are SEM images of sputtered $MoO_3$ deposited on alumina (FIGS. 9a–b) and a gold electrode (FIG. 9c).

The morphology of the sputtered films deposited on the alumina substrate is as shown in the SEM micrographs of FIG. 9. As shown in FIG. 9a, the film consisted of plate-like structures, which were made up of fine $MoO_3$ grains. These plate-like structures formed dense agglomerates. The pore sizes in these agglomerates ranged from 50–100 nm. These platelets grew spirally, forming steps as shown in FIG. 9b. The films near the gold-alumina interface showed a peculiar needle-like growth as depicted in FIG. 9c. The $MoO_3$ whiskers were found to be typically 80–100 μm long, and their diameter varied between 500 nm –1 μm. The absence of whisker structures in the part of $MoO_3$ films grown on alumina suggest that Au promotes the oxide growth along a preferred orientation or played a role in facilitating polymorphic reactions in which the stable phase ($\alpha$-$MoO_3$ in this case) grew in a rod-like form.

Figure 10:
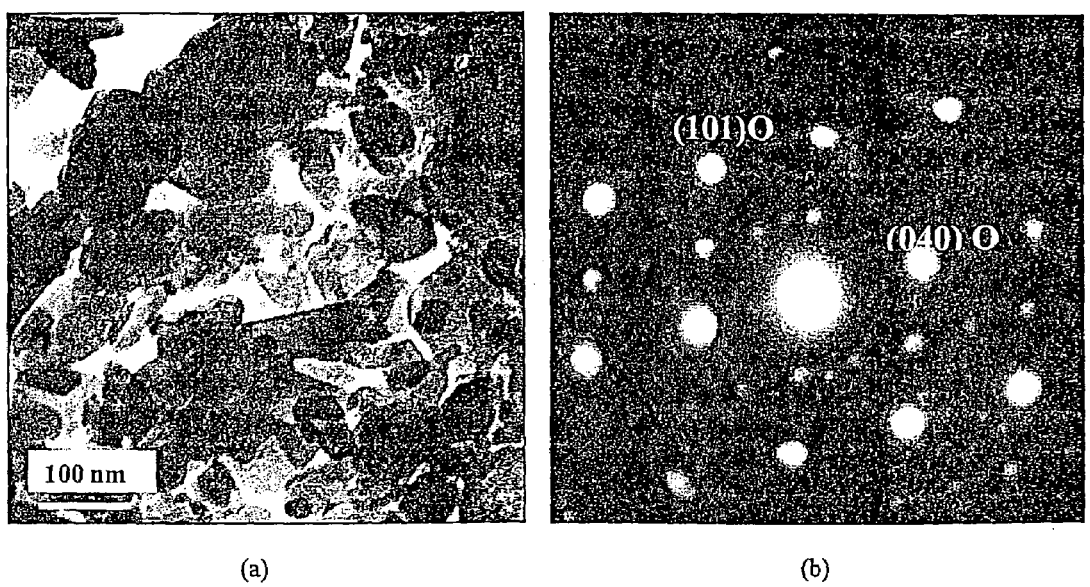
FIG. 10 includes a TEM image of sputtered and heat-treated $MoO_3$ (FIG. 10a), and a selected area diffraction pattern revealing the orthorhombic structure of the $MoO_3$ film (FIG. 10b).

FIG. 10a is a bright field transmission electron micrograph showing the grain structure of a sputtered and heat-treated $MoO_3$ film. The average grain size was calculated to be 85 nm. FIG. 10b shows a selected area diffraction pattern in which a particular crystallographic direction of the orthorhombic phase of $MoO_3$ was revealed. The brightest spots in the pattern originated from a grain oriented along this particular zone axis; however, superimposed in the pattern were diffraction spots originating from the surrounding grains having different relative orientation.

Figure 11:
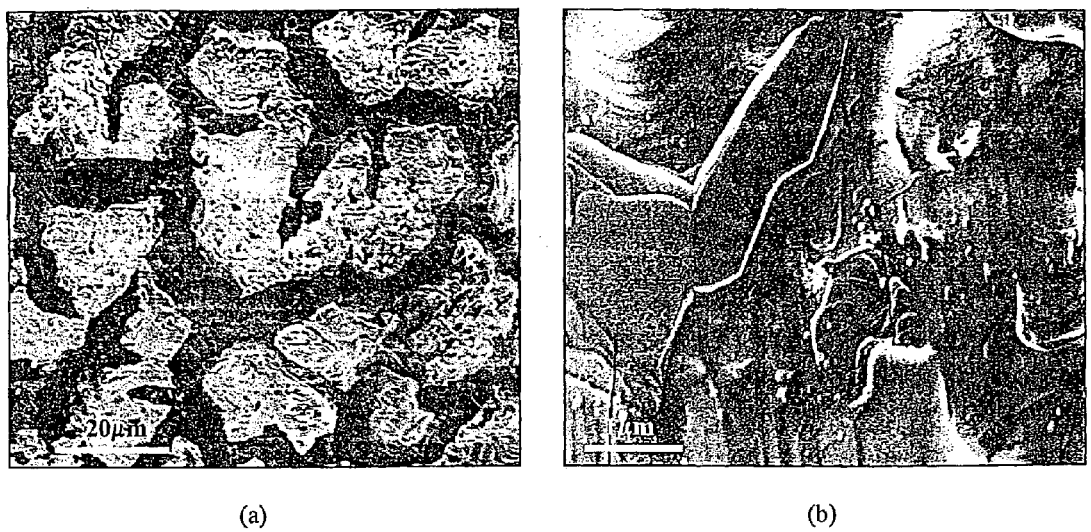
FIG. 11 includes SEM micrographs of sol-gel processed $MoO_3$ films (FIG. 11a) and heat-treated $MoO_3$ films (FIG. 11b) used for sensing.

The morphology of the sol-gel films was uniform throughout the area of the sensor and was composed of discrete "blocks" as shown in FIG. 11a. The pore sizes of these blocks were of the order of a few microns. These blocks were aggregates of smaller grains and grew in a step pattern (FIG. 11b) similar to that of sputtered samples on alumina. Cracks were a general feature in sol-gel samples due to stress created upon drying, resulting in poor binding with the substrate. Needle-like growth was absent in sol-gel $MoO_3$ near the gold electrodes.

Oxide needles (whiskers) were absent in sol-gel samples but were present in the sputtered material. Sputtering might induce growth along a preferred orientation on metallic stabilizers such as gold. The kinetics of polymorphic reactions in $MoO_3$ upon heat treatment is likely to be different for the sol-gel and the sputter-processed films, due to particle size effects. The observed needle growth effects might result from a phase reaction between two polymorphs, promoted by the presence of Au. This kind of growth is likely to be suppressed in sol-gel specimens due to the ultrafine grain sizes of the as-received microstructures, which favors metastable phase stabilization.

Example 6

Films produced in accordance with Examples 3 and 4 were then tested for their sensitivity to specific gases. The primary gases tested were ammonia and nitrogen dioxide. The gases were controlled through 1479 MKS Mass flow controllers (MKS, Andover, Mass.). The combined flow rate of the gases in the presence of either $NH_3$ or $NO_2$ was maintained at 1000 sccm. The gas mixture was passed through a Lindberg/Blue tube furnace (Lindberg, Watertown, Wis.), which was heated at a programmed rate. The sensor was placed inside the tube furnace within a quartz tube (1" diameter and 24" length) and was electrically connected to outside leads using gold wires. Sensing experiments were carried out at 450° C. Electrical resistance measurements of the sensing films as a function of the gas concentration were carried our using an Agilent 34401 digital multimeter (Agilent Technologies, Palo Alto, Calif.).

Figure 12A:
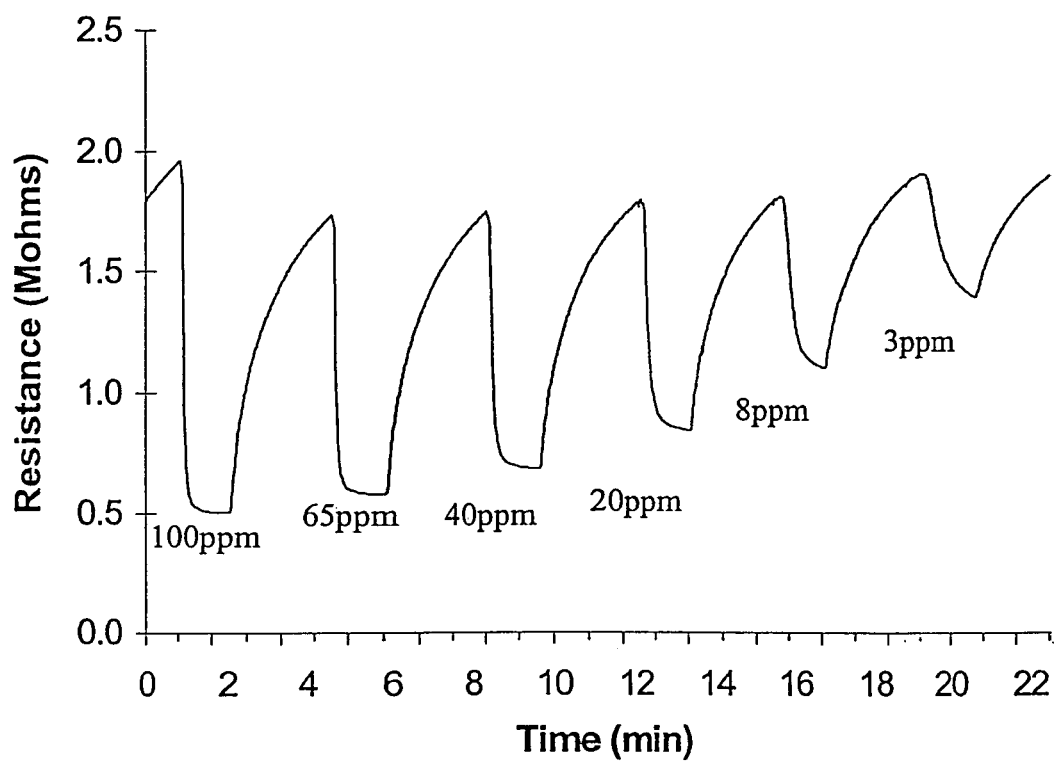
(FIG. 12a), and nitrogen dioxide at 450° C.
Figure 12B:
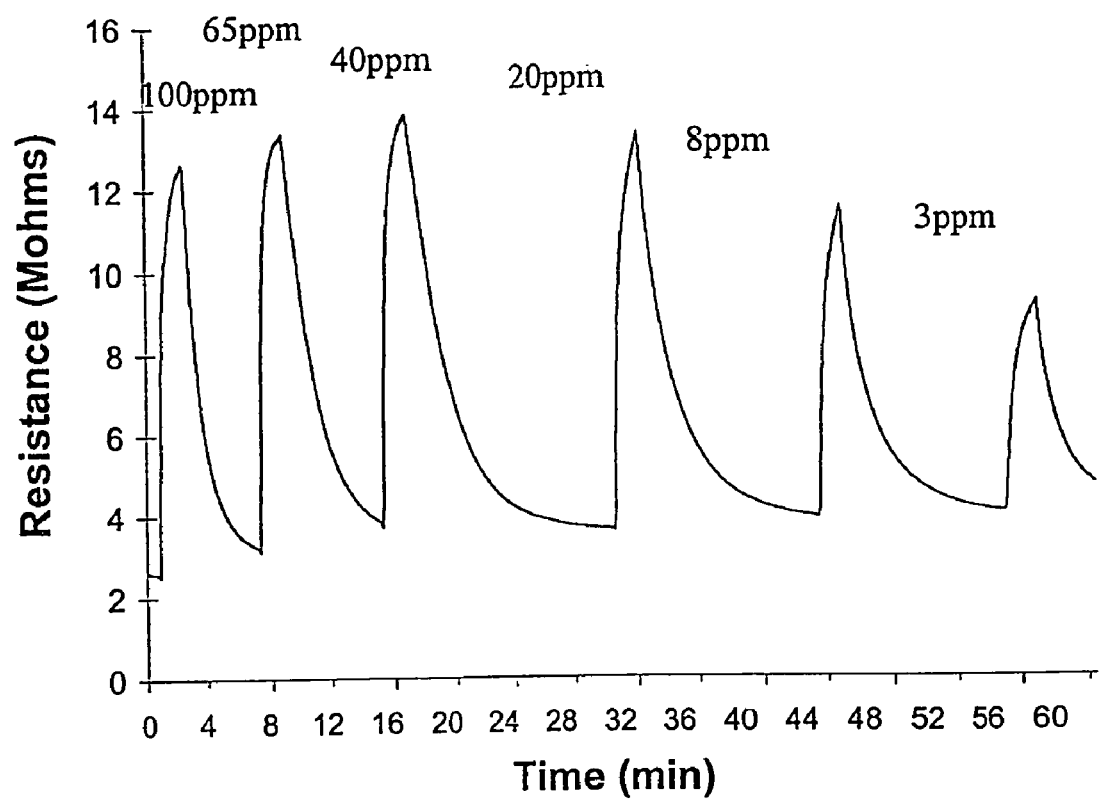
(FIG. 12b).

The response of ion beam deposited $MoO_3$ to ammonia and nitrogen dioxide is shown in FIGS. 12a–b, respectively. As seen from the graphs, sputtered $MoO_3$ was sensitive to both ammonia and nitrogen dioxide. In FIG. 12a, the resistance was plotted against time for various concentrations of ammonia in the secondary y-axis and time in the x-axis. The concentration of ammonia varied from around 100 ppm down to 3 ppm, with a background gas containing 12±3% oxygen and the remainder nitrogen. Ammonia being a reducing gas, the resistance of the film decreased when ammonia was passed over it and the resistance drop was proportional to the concentration of ammonia. The response time was rapid, a few seconds, and the recovery time was also fast, on the order of 2–3 minutes.

As set forth in FIG. 12b, under $NO_2$ exposure, which is an oxidizing gas, the resistance of the film increased. $NO_2$ concentration was varied from around 100 ppm down to 3 ppm. In this case the recovery times were long, 5–15 minutes. There appeared to be a reverse trend in resistance change at higher $NO_2$ concentrations, which may have been caused by the presence of residual $NH_3$ gas in the chamber from prior testing.

Example 7

Figure 13A:
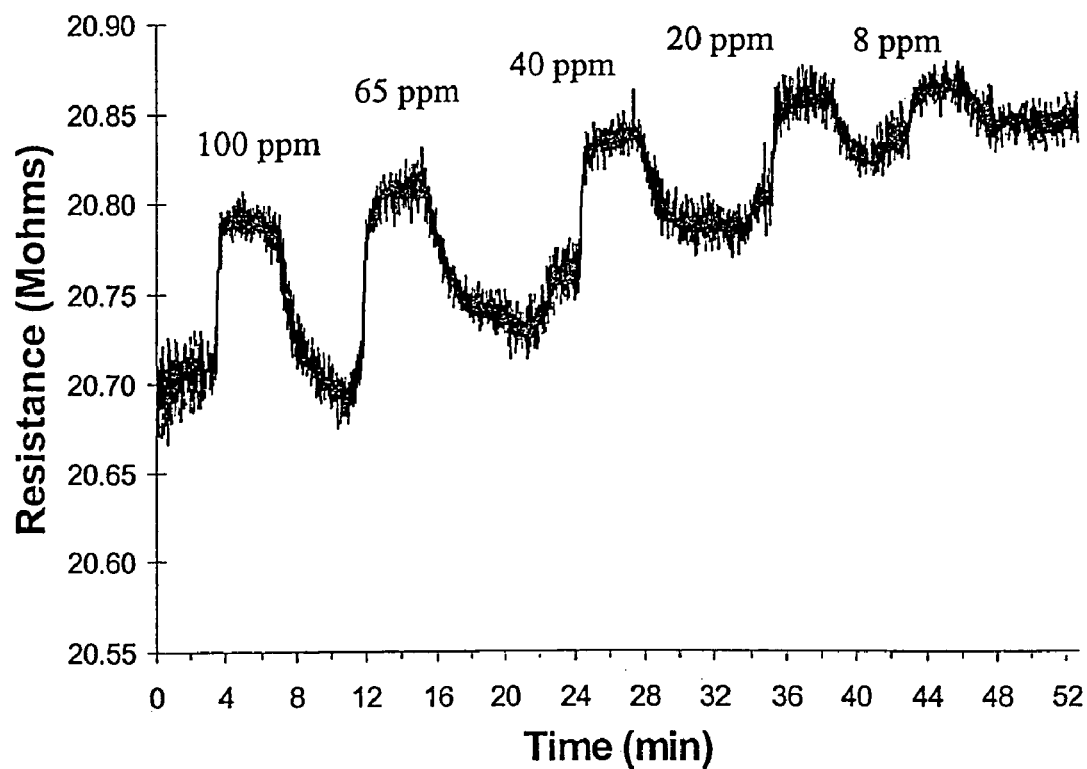
FIGS. 13a and 13b are graphs of the response of sol-gel $MoO_3$ films to $NH_3$ (from 100 ppm to 8 ppm) after heat treatment at 500° C. for 1 hour (FIG. 13a) and 8 hours (FIG. 13b).
Figure 13B:
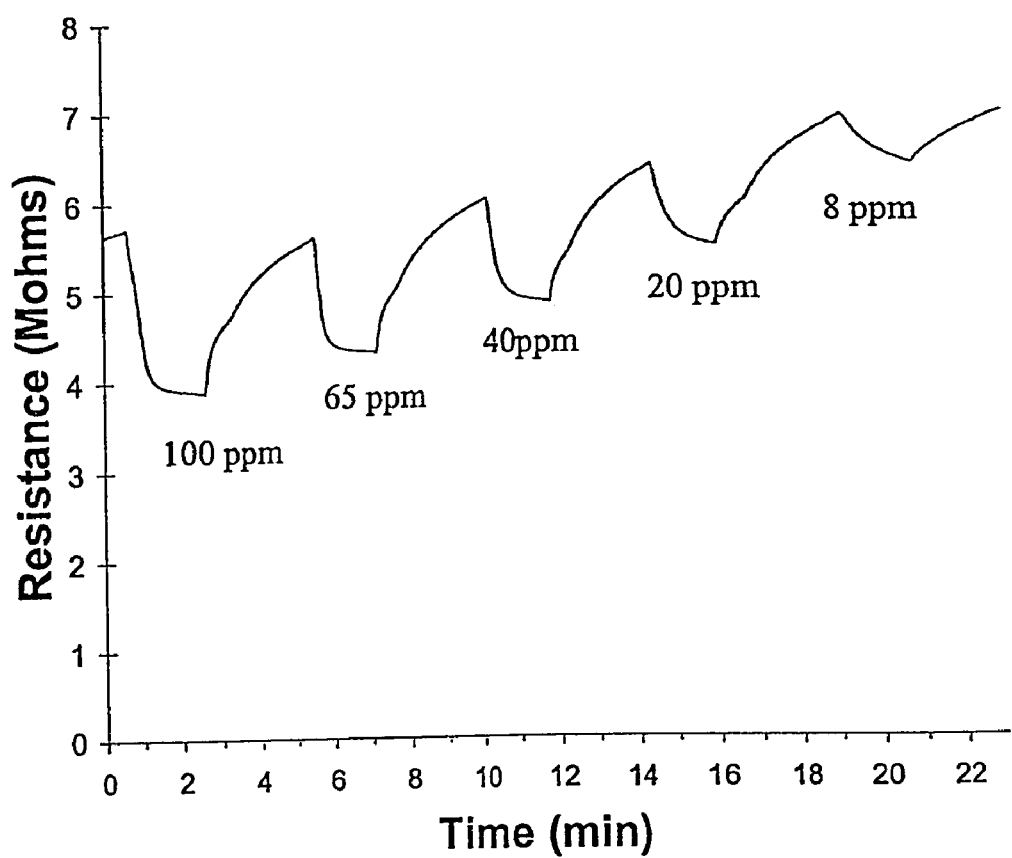

The response of sol-gel $MoO_3$ films to $NH_3$ and $NO_2$ were then obtained after heat treatment at 500° C. for a) 1 hour and b) 8 hours utilizing the sensing procedures and equipment described in Example 6. The plots in FIG. 13 show the response to ammonia after 1 hour (FIG. 13a) and 8 hours (FIG. 13b). From FIG. 13a, the response time was about 20–30 seconds and the recovery time was 5–7 minutes. It is interesting to note that the resistance increased on exposure to ammonia for the sample stabilized at 500° C. for 1 hr only (FIG. 13a). The observed n to p-type transition in the semiconducting behavior of the $MoO_3$ films could be due to phase variation, defects (both electronic and atomic), or formation of non-stoichiometric oxides. However, after heat treatment for 8 hours, a regular trend in response was observed as shown in FIG. 13b. The tests performed on the sensor heat treated for 8 hours showed only n-type response. The response and recovery times were 15–20 seconds and 2 minutes, respectively, for the samples heat-treated for 8 hours.

Figure 13C:
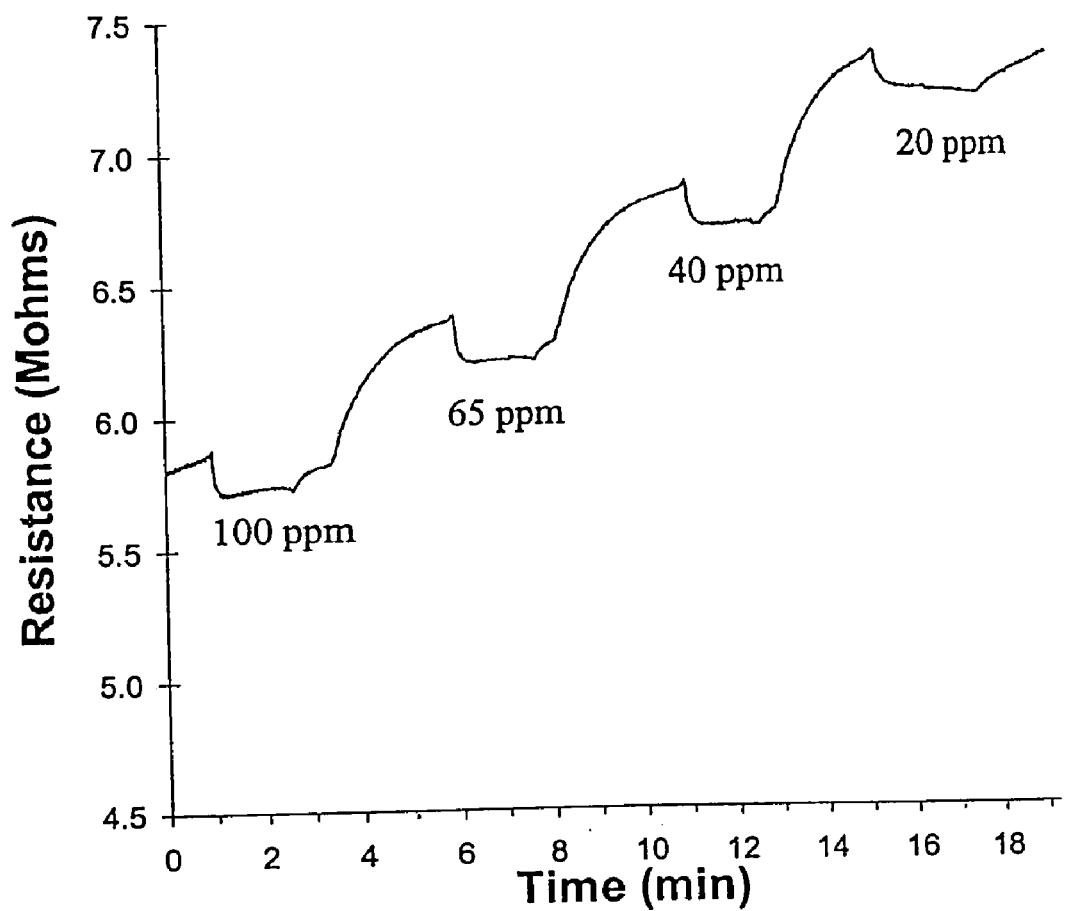
FIG. 13c is a graph of the response of sol-gel $MoO_3$ films to $NO_2$ (from 100 ppm to 20 ppm) after heat treatment at 500° C. for 8 hours.

The response to $NO_2$ showed similar behavior both after 1 hour and after 8 hours of heat stabilization at 500° C. The response of the sensor stabilized at 500° C. for 8 hours is shown in FIG. 13c. The drift in resistance of the sol-gel films may be due to the structural rearrangement of the films.

Figure 14:
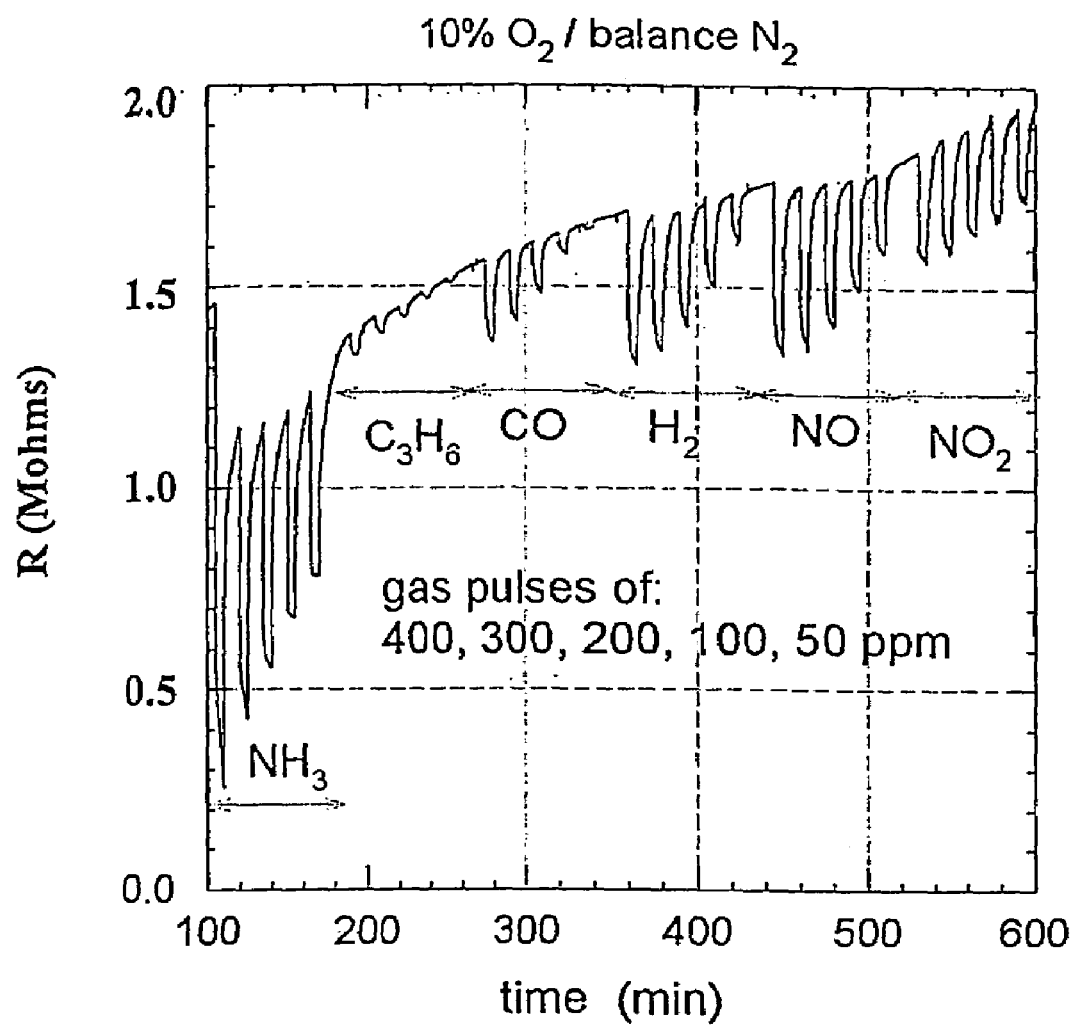
FIG. 14 illustrates the relative response of sol-gel processed $MoO_3$ films stabilized at 500° C. for 8 hours with respect to sensing ammonia, $C_3H_6$, CO, NO, $NO_2$, and $H_2$ in various concentrations (500 ppm to 50 ppm) at 462° C.

FIG. 14 illustrates the relative response of sol-gel processed films stabilized at 500° C. for 8 hours with respect to sensing ammonia, $C_3H_6$, CO, NO, $NO_2$, and $H_2$ in various concentrations (500 ppm to 50 ppm) at 462° C. There was a clear trend of selective response to ammonia in the presence of interfering gases.

Example 8

Thermoelectric tests were performed on the sol-gel processed samples heat-treated for 1 hour and those heat-treated for 8 hours. One end of the film was heated and the voltage was measured across the hot and the cold ends using an Agilent 34401 digital multimeter (Agilent Technologies, Palo Alto, Calif.). The positive end of a voltmeter was connected to the hot end and the negative connected to the cold end of the film. A negative reading in the voltmeter confirmed p-type behavior and a positive reading confirmed n-type behavior. The $MoO_3$ films heat-treated for 1 hour showed a mixed p and n type character when sampled at different areas. Hence, the sensing response obtained for films heat-treated for 1 hour may be due to mixed signals from several $MoO_3$ polymorphs or from the presence of non-stoichiometric oxide components.

Example 9

Tungsten trioxide films were prepared by dual ion beam deposition. The sputtering system described above in Example 1 was utilized with a tungsten target (CERAC, 99.9%) in combination with oxygen in secondary plasma to produce the tungsten trioxide film.

Example 10

Sol-gel films were prepared by mixing tungsten isopropoxide and n-butanol to make 0.1M solutions. Mixing was done under nitrogen atmosphere and then the sol was subjected to ultrasonic agitation for 2 hours. The sol was then allowed to age for 24 hours. A yellow transparent liquid was obtained after aging. The sol was dropped on sensor substrates made of alumina with gold interdigitated electrodes and spun at 2500 rpm for 30 seconds in a spin coater (Chemat Technology, KW-4A from Chemat Technology, Inc., Northridge, Calif.). In order to obtain thicker films of comparable thickness to those obtained by ion beam deposition, the spinning was repeated.

Example 11

Characterization of the films prepared in Examples 9 and 10 was carried out using Philips CM12 TEM (Philips Electronics, NV) with a $LaB_6$ cathode excited at 120 keV. The films were analyzed in the as-received state and after heat treatment at 500° C. for 8 hours. SEM studies were also performed on a LEO-1550 FEG SEM (Leo Electron Microscopy, Cambridge, UK) to understand the morphology of the films after testing. X-ray diffraction (XRD) analysis using a Philips ARD 3520 (Philips Electronics, NV) was also conducted to identify the phases present.

Sensing tests were carried out with nitrogen dioxide and ammonia gases with synthetic air (10% oxygen, nitrogen balance) in the background. The gases were controlled using 1479 MKS mass flow controllers (MKS, Andover, Mass.). The combined flow rate of the gases was maintained at 1000 sccm. A Lindberg/Blue tube furnace (available from Lindberg, Watertown, Wis.) was used for programmed heating and the resistance of the sensor monitored using an Agilent 34401 digital multimeter (Agilent Technologies, Palo Alto, Calif.). The sensor response was plotted as change in resistance versus time, with varying gas concentration.

Figure 15:
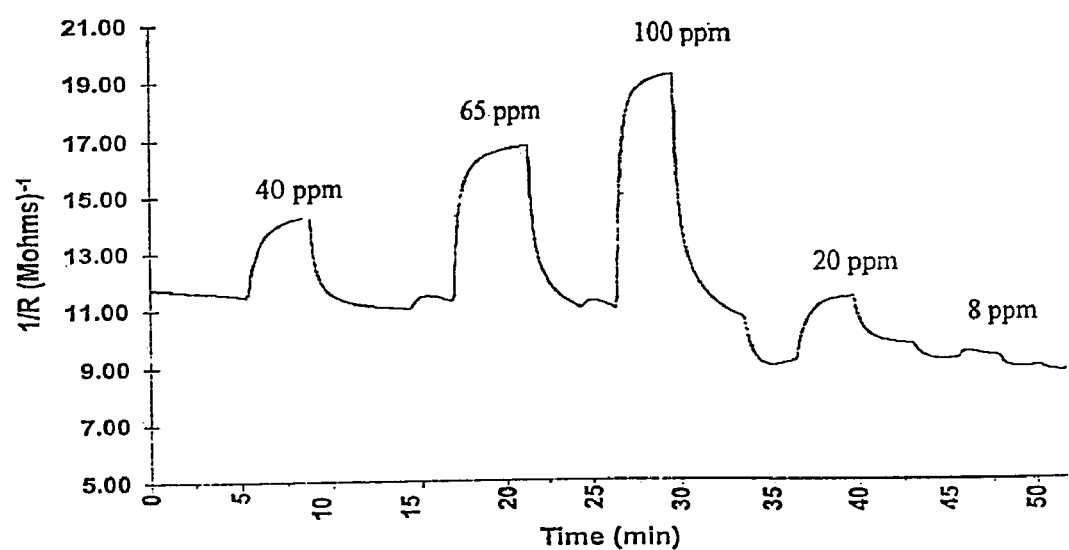
FIG. 15 is a graph depicting the response of ion beam deposited $WO_3$ to ammonia (from 100 ppm to 8 ppm).
Figure 16:
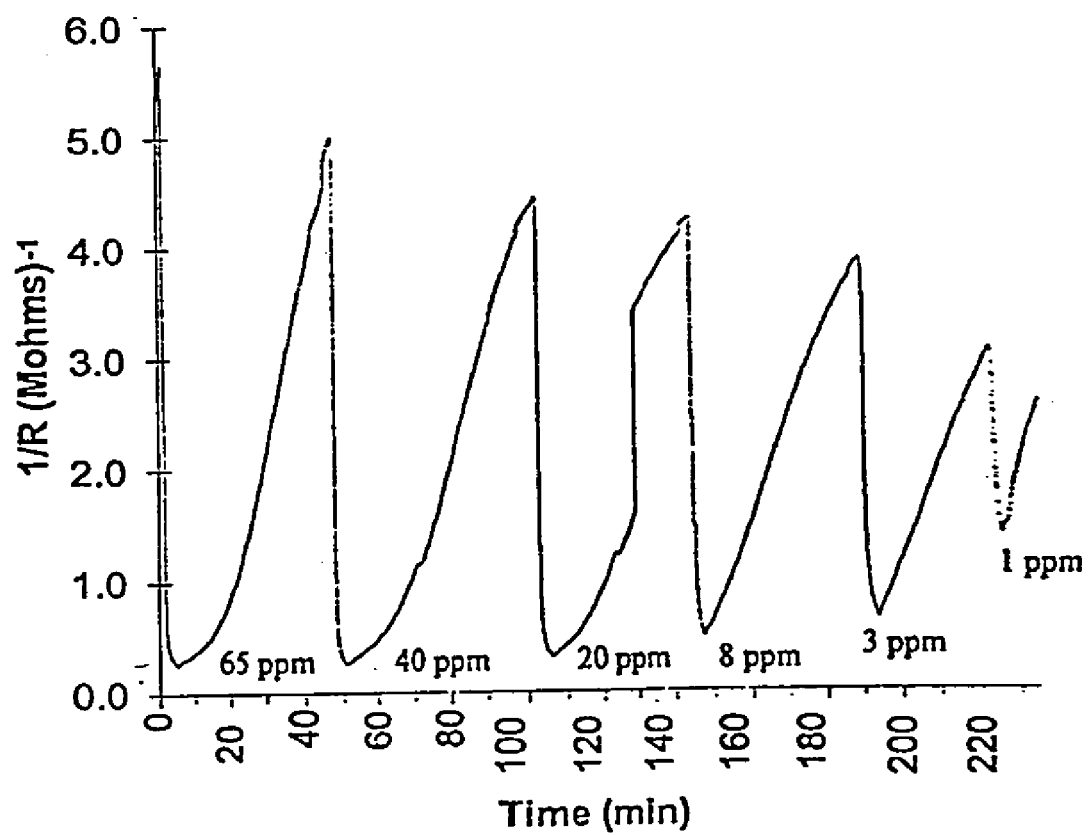
FIG. 16 is a graph depicting the response of ion beam deposited $WO_3$ to $NO_2$ (from 65 ppm to 1 ppm).

The response of the ion beam deposited $WO_3$ to ammonia and $NO_2$ at 450° C. is set forth in FIGS. 15 and 16, respectively. As can be seen from the graphs, $WO_3$ is highly sensitive to $NO_2$, even at low concentrations of 1 ppm. The response and recovery times were 10 seconds and 25–50 minutes, respectively. The adsorption of $NO_2$ on the surface of the $WO_3$ and possible slow desorption time may be responsible for the prolonged recovery time. The response to ammonia was negligible when compared to $NO_2$. Taking the sensitivity (defined as $\Delta R/R_{air}$) into account (10 times decrease for $NO_2$ as opposed to an increase of within 0.75 times for $NH_3$), $WO_3$ films prepared by ion beam deposition were selective towards $NO_2$ over $NH_3$.

Figure 17:
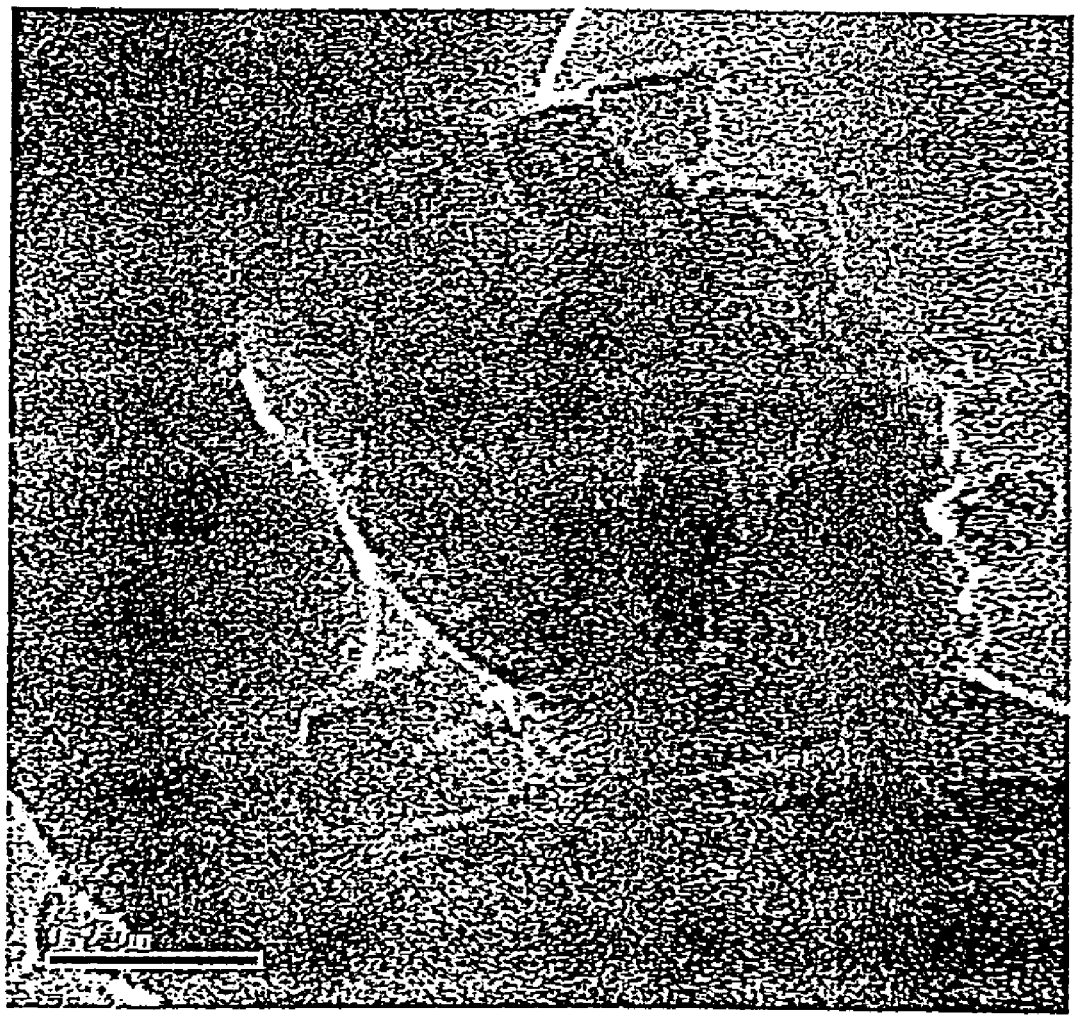
FIG. 17 is a TEM image of ion beam deposited $WO_3$ after the $WO_3$ film had been subjected to sensing tests.
Figure 18:
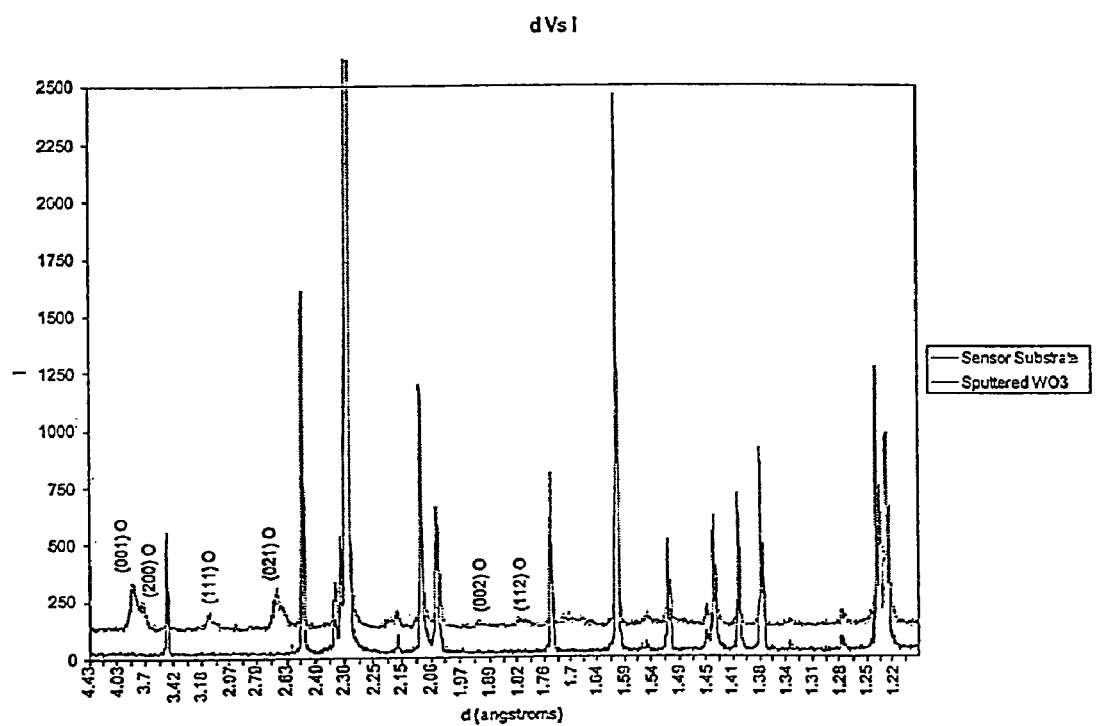
FIG. 18 is a graphical depiction of x-ray diffraction results after the $WO_3$ films had been subjected to sensing tests.

FIG. 17 is a transmission electron micrograph of ion beam deposited $WO_3$ after sensing experiments. The film was composed of tiny grains of 50 nm. XRD studies of the films after sensing, the results of which are set forth in FIG. 18, revealed the presence of orthorhombic phase in accordance with the data published by the Joint Committee on Powder Diffraction Standards (JCPDS) (now known as the International Centre for Diffraction Data, Newtown Square, Pa.) in powder diffraction file card number: 71–0131.

Example 12

Incorporation of urease in sol-gel matrix to detect urea Sol-gel films of $MoO_3$ were prepared as described above in Example 4. Urease was incorporated into the heat-treated sol-gel matrix as follows:

10 mg/ml of urease was prepared from Jack Beans obtained from Sigma-Aldrich (St. Louis, Mo.). 50 mg of 16000 units/g solid urease was dissolved in 5 ml of deionized water. The solution was ultrasonically agitated for 10 minutes. 25 μM of this solution was pipetted out (using Eppendorf micropipettes) and dropped over each of the sensors. The samples were then refrigerated (4° C.) for 24 hours. After 24 hours, another top layer of $MoO_3$ was spun on the substrates without heat treatment following the process set forth above in Example 4. They were allowed to hydrolyze inside the refrigerator (to preserve the urease) for 2 days. To detect ammonia, urea solution was dropped onto the sol-gel-urease-sol-gel sandwich. Urea solution was prepared by dissolving urea in water to obtain 20 mM solution. An example of such a sensor is set forth in FIG. 20.

It will be understood that various modifications may be made to the embodiments disclosed herein. Therefore, the above description should not be construed as limiting, but merely as exemplifications of preferred embodiments. For example, other metal oxides may be utilized in forming the thin film metal oxides utilized in the sensors described herein. Depending upon the metal oxide utilized, a sensor may be constructed with selectivity to a specific gas, with different thin film metal oxides being more selective for different gases. Those skilled in the art will envision other modifications within the scope and spirit of the claims appended hereto.

What is claimed is:

1. A sensor for detecting gases comprising a substrate, plural electrodes, and an undoped thin film metal oxide having a thickness of from about 5 nm to about 500 nm in contact with each electrode, wherein the thin film metal oxide is of sufficiently high purity to exhibit a selective response in the form of an increase or a decrease in an electrical property of the thin film metal oxide in the presence of a specific oxidizing gas selected from the group consisting of $O_2$, NO and $NO_2$, wherein the metal oxide consists essentially of cubic $ReO_3$ structured metal oxide selected from the group consisting of $WO_3$, $\beta$-$MoO_3$ and $UO_2$ and is selectively responsive to the oxidizing gases.

2. The sensor of claim 1, wherein the plural electrodes consist of at least two electrodes in communication with the thin film metal oxide and wherein said thin film metal oxide and electrodes are arranged so as to be capable of being contacted with a specific gas.

3. The sensor of claim 1, wherein the sensor incorporates a temperature sensing means.

4. The sensor of claim 1, wherein the substrate is selected from the group consisting of $Si/SiO_2$, SiC, GaN, and $Al_2O_3$.

5. The sensor of claim 1, wherein the electrodes are selected from the group consisting of gold, silver, tungsten, chromium, and titanium.

6. A method for determining the presence of a specific gas in a gaseous mixture which comprises providing a gas sensor with plural electrodes, each electrode in contact with a thin film metal oxide having a thickness of from about 5 nm to about 500 nm which exhibits an increase or a decrease in an electrical property of the thin film metal oxide in the presence of the specific gas, contacting the sensor with the gaseous mixture, detecting the increase or decrease in the electrical property by the electrodes, measuring the change in electrical property, and determining the specific gas concentration, wherein the specific gas is an oxidizing gas selected from the group consisting of $O_2$, NO and $NO_2$, wherein the metal oxide consists essentially of cubic $ReO_3$ structured metal oxide selected from the group consisting of $WO_3$, $\beta$-$MoO_3$ and $UO_2$ and is selectively responsive to the oxidizing gases.

7. The method of claim 6, the plural electrodes further comprising at least two electrodes in communication with the thin film metal oxide, and contacting the thin film metal oxide and the electrodes with the same gaseous mixture.

8. The method of claim 6, further comprising providing the thin film metal oxide with a porosity and increasing surface area for contact with the gaseous mixture.

9. The method of claim 6, wherein the measuring further comprises measuring the resistance of the sensor.

10. The method of claim 6, wherein the measuring further comprises measuring the capacitance of the sensor.

11. The method of claim 6, wherein the measuring further comprises measuring the impedance of the sensor.

12. The method of claim 6, wherein the sensor further comprises a substrate.

13. The method of claim 12, wherein the substrate is selected from the group consisting of Si/$SiO_2$, SiC, GaN, and $Al_2O_3$.

14. The method of claim 6, wherein the electrodes are selected from the group consisting of gold, silver, tungsten, chromium, and titanium.

* * * * *